United States Patent
Denis et al.

(10) Patent No.: US 10,351,539 B2
(45) Date of Patent: Jul. 16, 2019

(54) MACROCYCLIC COMPLEXES, THEIR PROCESS OF PREPARATION AND USE AS PET IMAGING AGENTS

(71) Applicants: INSTITUT NATIONAL DE LA SANTE ET DE LA RECHERCHE MEDICALE (INSERM), Paris (FR); UNIVERSITE D'AUVERGNE CLERMONT I, Clermont Ferrand (FR)

(72) Inventors: Claire Denis, Clermont-Ferrand (FR); Vincent Gaumet, Clermont-Ferrand (FR); Aurélien Vidal, Saint-Herblain (FR); Philippe Auzeloux, Clermont-Ferrand (FR); Jean-Claude Madelmont, Clermont-Ferrand (FR); Elisabeth Miot-Noirault, Clermont-Ferrand (FR); Jean-Michel Chezal, Clermont-Ferrand (FR)

(73) Assignees: INSERM (Institut National de la Santé et de le Recherche Médicale), Paris (FR); Université d'Auvergne Clermont 1, Clermont Ferrand (FR)

( * ) Notice: Subject to any disclaimer, the term of this patent is extended or adjusted under 35 U.S.C. 154(b) by 10 days.

(21) Appl. No.: 15/329,622

(22) PCT Filed: Jul. 28, 2015

(86) PCT No.: PCT/EP2015/067318
§ 371 (c)(1),
(2) Date: Jan. 27, 2017

(87) PCT Pub. No.: WO2016/016272
PCT Pub. Date: Feb. 4, 2016

(65) Prior Publication Data
US 2017/0210714 A1   Jul. 27, 2017

(30) Foreign Application Priority Data
Jul. 28, 2014   (EP) .................................... 14306211

(51) Int. Cl.
*C07D 257/02*   (2006.01)
*C07F 1/08*      (2006.01)
*C07D 487/08*   (2006.01)

(52) U.S. Cl.
CPC ......... *C07D 257/02* (2013.01); *C07D 487/08* (2013.01); *C07F 1/08* (2013.01)

(58) Field of Classification Search
CPC ............................... C07D 257/02; C07F 1/08
See application file for complete search history.

(56) References Cited

FOREIGN PATENT DOCUMENTS

WO         01/00621 A1      1/2001

OTHER PUBLICATIONS

Clark. Frontiers in Immunology, 2013, 4, 1-4 (Year: 2013).*
Hettich. Journal of the American Chemical Society, 1997, 119, 5638-47 (Year: 1997).*
Colette et al., "Synthesis of N-quaternary ammonium [3H] and [99mTc]polyazamacrocycles, potential radiotracers for cartilage imaging", Journal of Labelled Compounds and Radiopharmaceuticals, May 1, 2000, pp. 585-594, vol. 43, No. 6.
Serdons et al., "Developing new molecular imaging probes for PET", Methods, Jun. 1, 2009, pp. 104-111, vol. 48, No. 2.

* cited by examiner

*Primary Examiner* — Noble E Jarrell
(74) *Attorney, Agent, or Firm* — W & C IP

(57) ABSTRACT

The present invention concerns compounds of formula (I): their process of preparation and compositions thereof. The present invention also concerns their use as diagnostic agent in PET imaging.

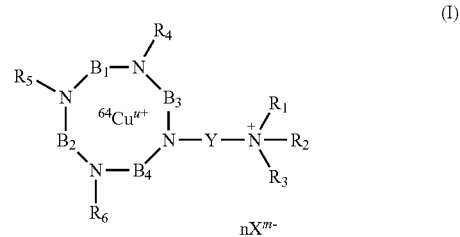

13 Claims, 1 Drawing Sheet

MACROCYCLIC COMPLEXES, THEIR PROCESS OF PREPARATION AND USE AS PET IMAGING AGENTS

FIELD OF THE INVENTION

The present invention concerns new macrocyclic complexes, their process of preparation, solutions and pharmaceutical compositions thereof.

The present invention also concerns a kit comprising components necessary for forming said macrocyclic complexes.

The present invention also concerns said novel macrocyclic complexes useful as diagnostic agents, in particular in Positron Emission Tomography (PET) imaging, and specifically for the diagnosis and/or the therapeutic follow-up of diseases associated with a deregulation of the proteoglycan concentration.

BACKGROUND OF THE INVENTION

The loss or the overexpression of proteoglycans constitutes a physiopathological biomarker of several cartilage degenerative pathologies such as osteoarthritis, arthritis, intervertebral disk diseases as well as aneurysm or aortic dissection. Overexpression of proteoglycans is also encountered in chondrosarcoma, a malignant tumor composed of cartilage-producing cells.

Due to the ageing population, cartilage degenerative pathologies such as osteoarthritis, set serious public health issues in developed countries. Until now, the therapeutic management is only symptomatic. More than 14 million of prescriptions per year in France aim to reduce and control symptoms such as pain and functional discomfort.

Concerning osteoarthritis, there is consensus regarding the necessity of an early diagnosis, based on the perspective of disease modifying drugs for osteoarthritis (DMOAD). However, at an early stage, clinicians lack of objective, reliable and sensitive criteria for evaluating the progression of the disease.

The current gold standard method, based on the assessment of joint-space narrowing by X-ray techniques, is limited in terms of precision and sensitivity. Ding et al. (Nat. Clin. Pract. Rheumatol. 2008, 4, 4-5) report that knee cartilage volume is reduced more than 10% until the first radiographic abnormalities were detected.

MRI techniques and dosages with relevant biochemical markers have also been evaluated. These methods however lack of specificity and/or sensitivity, and are unable to detect slight biochemical modifications associated with osteoarthritis (Ding et al., Curr. Opin. Rheumatol. 2013, 25, 125-135). In another hand, current available radiotracers only explore bone remodeling metabolism (e.g. $^{99m}$Tc-hydroxymethylene diphosphonate, $^{99m}$Tc-HMDP) or inflammatory processes (e.g [$^{18}$F]-2-fluoro-2-deoxyglucose, [$^{18}$F]FDG).

With these conventional radiotracers, imaging techniques such as Single-Photon Emission Computed Tomography (SPECT, or less commonly, SPET) or Positron Emission Tomography (PET), eventually combined with X-ray Computed Tomography (SPECT-CT or PET-CT), only provide indirect information of the cartilage degradation during the late stages of the disease, namely the inflammation and alteration of the subchondral bone steps (Tremoda et al., EJNMMI Res. 2011, 1, 11).

Cancerous cartilage diseases (i.e. chondrosarcoma) represent 25% of the total primary malignant bone tumors diagnosed in humans. The tumor develops from chondrocytes and is thus rich in proteoglycans (PG). It can be found in multiple histological forms (grades 1, 2 or 3) which differ in terms of treatment and prognosis. The 5-year survival is 80% for chondrosarcoma of grade 1, 50% for chondrosarcoma of grade 2, and only 20% for chondrosarcoma of grade 3 (Angelini et al., J. Surg. Oncol. 2012, 106, 929-937).

Yet, there is a real expectation of clinicians in this domain, taking into account the low sensitivity or/and specificity of conventional imaging techniques such as radiography, scanner and MRI. One the one hand, CT and MRI define morphology, but are unable to distinguish postoperative or post-chemotherapeutic residual lesions due to altered tissue planes, edema and fibrosis. (Soldatos et al., J. Comput. Assist. Tomo., 2011, 35, 504-511; Logie et al., Semin Musculoskelet. Radiol. 2013, 17, 101-115). One the other hand, radiotracers currently available such as $^{201}$Tl, $^{99m}$Tc-MIBI, $^{99m}$Tc-Tetrofosmin, $^{99m}$Tc-DMSA(V) and $^{18}$F-FDG, provide indirect evaluations of the pathology, and have demonstrated their limitations for imaging chondrosarcoma with low cellularity and vascularity (Brenner et al., Eur. J. Nucl. Med. Mol. Imaging 2004, 31, 189-195; Murata et al., Ann. Nucl. Med. 2008, 22, 221-224; Douis et al., Skeletal Radiol. 2013, 42, 611). Therefore, there is an urgent need for markers that characterize biologic phenotypic features of the tumor to guide clinical decision making (Riedel et al., Curr. Treat. Options Oncol. 2009, 10, 94-106).

Proteoglycans (PG) constitute with collagen the essential biochemical components of the extracellular matrix (ECM) of connective tissues as cartilage. The proteoglycan matrix of chondrosarcoma is composed mainly of aggrecan-type proteoglycans. Aggrecan is a macromolecule made up of a core protein substituted with covalently linked glycosaminoglycan (GAG) chains.

According to literature, there are similarities between articular cartilage and intervertebral discs (IVD). Healthy IVD are comprised of three different areas: Annulus Fibrosus (AF) which surrounds the Nucleus Pulposus (NP), and the vertebral end plates embedding the AF and NP (Urban et al., Arthritis Research and therapy 2003, 5, 120-130). The few cells found in IVD are similar to articular chondrocytes, while the ECM of IVD and hyaline cartilage share the same main components: collagen and PG. As for articular cartilage, most of the PG found in IVD are aggrecans. Remodeling of both cells and PG of NP is considered to be relevant biomarkers of IVD degeneration at earlier stages of pathologies, associated with lumbar pain. Indeed, during IVD degeneration, the NP is the first component affected with i) an alteration and remodeling of the PG content leading to dehydration and disorganization of the ECM, and ii) a decrease of cell density (Lyons et al., Biochim. Biophys. Acta 1981, 673, 443-453; Antoniou et al., J. Clin. Invest. 1996, 98, 996-1003; Roughley et al., Spine 2004, 29, 2691-2699; Adams et al., Spine 2006, 31, 2151-2161; Clouet et al., Spine 2009, 76, 614-618).

However, imaging techniques conventionally used for the evaluation of this disease (X-ray, MRI and CT) also provide anatomic information (calcifications, radial cracks, disc pinching . . . ) only at very late stage (Sether et al., Radiology 1990, 177, 385-388; Pfirrmann et al., Spine 2001, 26, 1873-1878; Finch et al., Nat. Clin. Pract. Rheumatol. 2006, 2, 554-561).

Other diseases, such as aneurysms and aortic dissections are characterized by the presence of mucoid degeneration and alcianophil areas rich in GAG (Houard et al., Pathology 2007, 212, 20-28; Sarda-Mantel et al., Arterioscler. Thromb.

Vasc. Biol. 2006, 26, 2153-2159; Roccabianca et al., Biomech. Model. Mechanobiol. 2014, 13, 13-25).

For above pathologies, measuring PG disorders (loss or overexpression) could permit early diagnosis and also assessment of extent, longitudinal follow-up of treated patients and evaluation of new therapies.

Because of the high sulfate and carboxyl group content of their GAG moieties, PG have strong negative charges that have been shown to interact with the positively charged quaternary ammonium function (QA) (Gibbs-Strauss et al., Molecular Imaging, 2010, 9, 128; Maurizis et al., Biochem. Pharmacol. 1992, 44, 1927; Sidney Yu et al., Int. J. Rad. App. Instrum. B, 1989, 16, 255)

French patent application FR 2 795 412 A1 discloses compounds with a strong affinity for cartilage tissues containing quaternary ammonium function of the following formula:

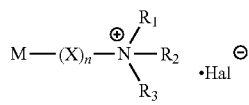

wherein M represents a molecule useful in the treatment or diagnosis of diseases caused by cartilage damage, notably as radiotracer. More specifically, this document reports $^{99m}$Tc-NTP 15-5 complex having the following formula:

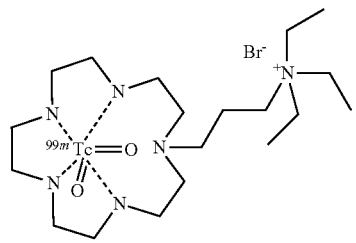

which exhibits a high uptake in the PG-rich tissues after intravenous injection (i.v.). Since this statement has been reinforced by articular cartilage imaging (Ollier et al., J. Nucl. Med. 2001, 42, 141-145; Miot-Noirault et al., Eur. J. Nucl. Med. Mol. Imaging 2007, 34, 1280-1290; Miot-Noirault et al., Molecular Imaging 2008, 7, 263-271) and chondrosarcoma imaging studies (Miot-Noirault et al., J. Nucl. Med. 2009, 50, 1541-1547; Peyrode et al., Sarcoma, 2011, Article ID691608, 8 pages; Miot-Noirault et al., EJNMMI Res. 2013, 3, 40).

SPECT imaging is limited in terms of sensitivity and quantitative performances and thus is little suitable for early diagnosis and/or follow-up of pathologies involving cartilage degeneration such as osteoarthritis, arthritis or chondrosarcoma.

PET imaging appears to be more appropriate to solve the above-mentioned issues. Radiotracers for PET imaging require radioisotope elements that emit positrons, whose annihilate to produce two photons with opposite direction. Radioisotope elements used for radiotracers within PET include notably $^{124}$I, $^{68}$Ga, $^{64}$Cu, $^{18}$F, $^{15}$O, $^{13}$N, or $^{11}$C (Serdons, K, Verbruggen, A, Bormans, G. M. Developing new molecular imaging probes for PET. *Methods* 2009, 48, 104-111).

Such radioactive compounds could be used to explore physiological and pathological processes within the limits of several requirements, notably in terms of specific binding to target tissues, thermodynamic stability, in vivo kinetic inertness, adequate elimination (such as urinary clearance), low non-specific uptake in non-target tissues, availability, toxicity and appropriate radioactive isotope so as to ensure good target to non-target contrast.

Two kinds of radiotracers are currently known:

(1) chemical compounds in which one or more atoms have been replaced by a non-metallic radioelement (i.e. $^{124}$I, $^{18}$F, $^{15}$O, $^{13}$N, $^{11}$C . . . ), like $^{18}$F-FDG, (2) bifunctional chelators (BFC) referred herein to compounds made up of a chelating ligand for chelation of metallic radioelement (i.e. $^{68}$Ga, $^{64}$Cu . . . ) through coordinate covalent bonds, linked to a functional group that can be used for attachment to a targeted molecule (e.g. antibodies, peptides, proteins). One of the BFC's advantages is that the chemistry of conjugation can preserve the structural integrity of the targeted molecule as no extremes of temperature or pH are required.

The estimation of the overall complex charge for new radiolabelled BFC, which is a key parameter when developing PG-targeting radiotracers, must be assessed case by case.

Even if complex stability forecasting and in vitro complex stability measurements give an accurate starting point, they can be questioned by in vivo experiments (I. Sin et al., Bioorg. Med. Chem. 2014, 22, 2553-2562).

If numerous studies deal with radiotracer for PET imaging, none has been reported on targeting cartilage PG specifically. As shown previously, there is a need for a non-invasive method evaluating integrity and functionality of cartilage and allowing an early diagnosis, a longitudinal follow-up and evaluation of therapy response for diseases associated with a deregulation of the proteoglycan concentration such as osteoarthritis, arthritis, chondrosarcoma, IVD degeneration or aneurysm and aortic dissection.

There is therefore a need for diagnostic agents that are able to target proteoglycans and are suitable for use within PET imaging.

SUMMARY OF THE INVENTION

The present invention thus aims to provide new compounds that show a strong affinity for proteoglycans and are useful as diagnostic agents for PET imaging.

Another aim of the present invention is to provide said compounds for use as a diagnostic agent.

A further aim of the present invention is to provide pharmaceutical compositions, notably diagnostic agents, comprising said compounds.

A further aim of the present invention is to provide solution, such as aqueous solution, comprising said compounds.

Yet another aim of the present invention is to provide said compounds for use in the diagnosis and/or the therapeutic follow-up and/or the treatment of diseases associated with deregulation of the proteoglycan concentration.

A further aim of the present invention is to provide a process for the preparation of said compounds.

A further aim of the present invention is to provide a kit for preparing said compounds.

The invention is based on the finding that QA attached to polyazamacrocycles have a strong affinity towards proteoglycans and form with $^{64}$Cu, radiolabelled complexes which are useful as diagnostic agents for PET imaging.

DESCRIPTION OF THE INVENTION

According to the invention, there are thus provided compounds having the following formula (I):

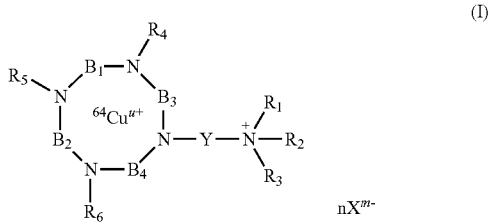

wherein:

$R_4$, $R_5$ and $R_6$ are independently of each other, chosen from the group consisting of: H, $-(CH_2)_p COOR'$, $-(CH_2)_p Ar$, $-(CH_2)_p Het$ and an alkyl group linear or branched comprising from 1 to 10 carbon atoms, wherein:

R' represents H, an alkyl group linear or branched comprising from 1 to 10 carbon atoms, or an aryl group comprising from 6 to 20 carbon atoms;

p and q are, independently of each other, an integer comprised from 0 to 10, preferably from 0 to 5, and more preferably from 1 to 2;

Ar represents an aryl group comprising from 6 to 20 carbon atoms;

Het represents a heteroaryl comprising from 5 to 20 atoms;

$R_1$, $R_2$ and $R_3$ represent, independently of each other, an alkyl group, linear or branched, comprising from 1 to 10 carbon atoms, or an aryl group comprising from 6 to 20 carbon atoms;

or $R_1$, $R_2$ and $R_3$ together with the nitrogen atom carrying them, form a saturated or unsaturated nitrogen-containing heterocycle, said heterocycle being optionally substituted;

or $R_4$ and $R_5$ may form together, with the nitrogen atoms carrying them, a heterocycle group comprising from 4 to 20 atoms, said heterocycle group optionally comprising at least one heteroatom chosen from O, N and S;

or $R_4$ and $R_6$ may form together, with the nitrogen atoms carrying them, a heterocycle group comprising from 9 to 40 atoms, said heterocycle group optionally comprising at least one heteroatom chosen from O, N and S;

$B_1$, $B_2$ and $B_4$ represent, independently of each other, an alkylene group comprising from 2 to 10 carbon atoms, preferably from 2 to 5, and more preferably from 2 to 3 carbon atoms, said alkylene group being linear or branched;

$B_3$ represents

wherein:

r, s and t are, independently of each other, an integer comprised from 0 to 10, preferably from 0 to 5;

$R_7$ is chosen from the group consisting of: H, $-(CH_2)_p COOR'$, $-(CH_2)_p Ar$, $-(CH_2)_p Het$ and an alkyl group linear or branched comprising from 1 to 10 carbon atoms, wherein R', Ar, Het, p and q are as defined above;

Y represents an alkylene group comprising from 1 to 10 carbon atoms, preferably from 1 to 6, and more preferably 3 carbon atoms;

u represents an integer comprised from 0 to 4, preferably 2;

n represents an integer comprised from 1 to 6, preferably from 1 to 4;

$X^{m-}$ is a conjugate base of an acid, m representing an integer comprised from 1 to 4;

n, m and u being such that the total charge of the compound of formula (I) is zero, or their pharmaceutically acceptable salts, or hydrates.

It is well known that the stability of a complex may be affected by the substitution of the radionuclide. For example, Boros et al. ("One to chelate them all: investigation of a versatile, bifunctional chelator for $^{64}Cu$, $^{99m}Tc$, Re and Co.", Dalton Trans., 2011, 40, 6253) discloses that the stability of di-picolyl-carboxylate (dip) complexes with $^{99m}Tc$ is better than the corresponding complexes with $^{64}Cu$. It also mentions that the dip complexes with $^{64}Cu$ are not sufficiently stable for in vivo applications.

Besides, it is also known that such metal substitution in a similar ligand may imply significant modifications in their pharmacokinetic profile. In particular, Thakur et al. ("Pet imaging of oncogene overexpression using $^{64}Cu$-vasoactive intestinal peptide analog: comparison with $^{99m}Tc$-VIP analog", The Journal of Nuclear Medicine, 2004, 45, p. 1381-1389) discloses in Table 2 that $^{64}Cu$-TP3982 leads to higher liver uptake than with $^{99m}Tc$-TP3982, and to higher concentration in non-target organs such as muscles, heat, lungs.

However, the inventors advantageously found that the macrocyclic ligands of the invention, for some of them used for $^{99m}Tc$ complexation, are also very useful for the chelating of $^{64}Cu$ leading to thermodynamically and kinetically stable radiocopper complexes in vivo.

The compounds of the invention ensure good target to non-target contrast, are rapidly eliminating from the body (good urinary clearance), specifically target proteoglycans. They advantageously allow a fast and a high uptake on cartilages (target organs), and low or undetectable uptake in non-target organs. The compounds of the invention are thus particularly suitable as diagnostic agent for PET imaging.

In particular, the nature of $nX^{m-}$ in the compounds of formula (I) depends on the nature of the buffer solution used for preparing the compounds of formula (I) and/or the nature of X of the $n'X^{m-}$ moiety in the compounds of formula (I') as defined later in the description.

The present invention also relates to compounds of formula (II):

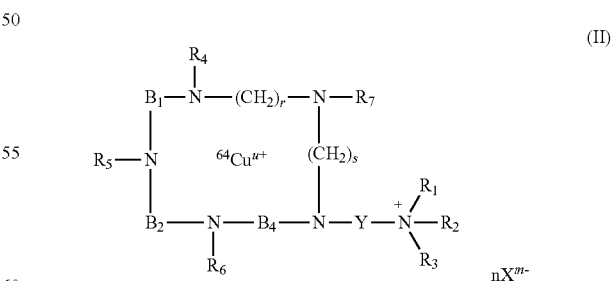

wherein $R_1$, $R_2$, $R_3$, $R_4$, $R_5$, $R_6$, $R_7$, Y, n, X, m, $B_1$, $B_2$, $B_4$, r, s and u are as defined above, or their pharmaceutically acceptable salts, or hydrates.

The compounds of formula (II) correspond to compounds of formula (I) wherein t is 1.

The present invention also relates to compounds of formula (III):

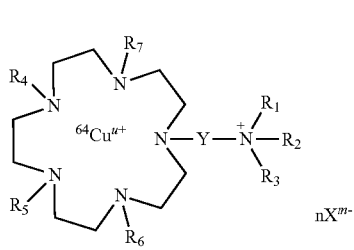

wherein $R_1$, $R_2$, $R_3$, $R_4$, $R_5$, $R_6$, $R_7$, Y, n, X, m and u are as defined above, or their pharmaceutically acceptable salts, or hydrates.

The compounds of formula (III) correspond to compounds of formula (I) wherein $B_1$, $B_2$ and $B_4$ represent —$CH_2CH_2$—, and $B_3$ represents —$CH_2CH_2$—$N(R_7)$—$CH_2CH_2$—.

Among the compounds of formula (III), preferred compounds are:

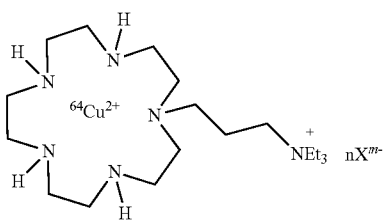

wherein $nX^{m-}$ is as defined above, and in particular $X^{m-}$ is selected from chloride ions, citrate ions and mixtures thereof. In particular, $nX^{m-}$ is $3Cl^-$ or $C_6H_5O_7^{3-}$.

The present invention also relates to compounds of formula (IV):

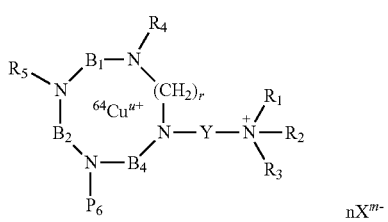

wherein $R_1$, $R_2$, $R_3$, $R^4$, $R_5$, $R_6$, Y, n, X, m, $B_1$, $B_2$, $B_4$, r and u are as defined above, or their pharmaceutically acceptable salts, or hydrates.

The compounds of formula (IV) correspond to compounds of formula (I) wherein t is 0.

The present invention also relates to compounds of formula (V):

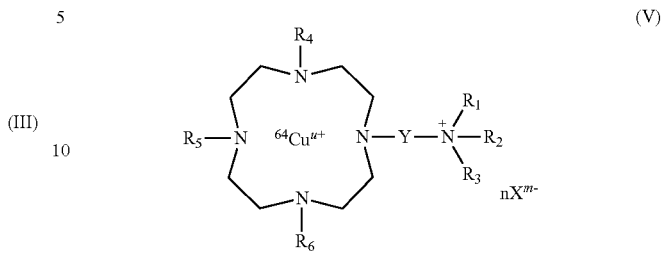

wherein $R_1$, $R_2$, $R_3$, $R_4$, $R_5$, $R_6$, Y, n, X, m and u are as defined above, or their pharmaceutically acceptable salts, or hydrates.

The compounds of formula (V) correspond to compounds of formula (I) wherein $B_1$, $B_2$, $B_3$ and $B_4$ represent —$CH_2CH_2$—.

The present invention also relates to compounds of formula (VI):

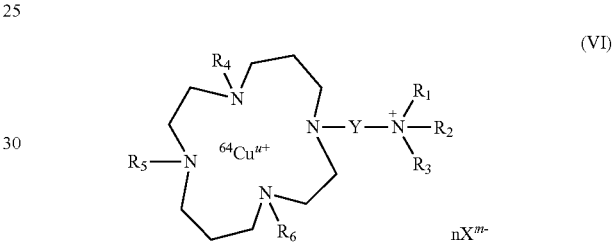

wherein $R_1$, $R_2$, $R_3$, $R_4$, $R_5$, $R_6$, Y, n, X, m and u are as defined above, or their pharmaceutically acceptable salts, or hydrates.

The compounds of formula (VI) correspond to compounds of formula (I) wherein $B_1$ and $B_4$ represent —$CH_2CH_2$—, and $B_2$ and $B_3$ represent —$CH_2CH_2$—$CH_2$—.

According to the present invention, in the formulae (I), (II), (III), (IV), (V) or (VI) above-mentioned, each of $R_4$, $R_5$ and $R_6$ may be identical or different.

According to an embodiment, in the formulae (I), (II), (III), (IV), (V) or (VI) above-mentioned, $R_4$, $R_5$ or $R_6$ is H.

According to an embodiment, in the formulae (I), (II), (III), (IV), (V) or (VI) above-mentioned, $R_4$, $R_5$ or $R_6$ is —$(CH_2)_p COOR'$, R' representing H, an alkyl group linear or branched comprising from 1 to 10 carbon atoms, or an aryl group comprising from 6 to 20 carbon atoms. In particular, R' represents H. In particular, R' represents an alkyl group linear or branched comprising from 1 to 10 carbon atoms, more preferably from 1 to 4 carbon atoms such as —$C(CH_3)_3$.

According to an embodiment, in the formulae (I), (II), (III), (IV), (V) or (VI) above-mentioned, $R_4$, $R_5$ or $R_6$ represents —$(CH_2)_q Ar$, Ar representing an aryl group comprising from 6 to 20 carbon atoms. In particular, Ar is a phenyl group. In particular, $R_4$, $R_5$ or $R_6$ represents —$CH_2Ph$, with Ph representing a phenyl group.

According to an embodiment, in the formulae (I), (II), (III), (IV), (V) or (VI) above-mentioned, $R_4$, $R_5$ or $R_6$ represents —$(CH_2)_q Het$, Het represents a heteroaryl group comprising from 5 to 20 atoms, preferably comprising 6 atoms. In particular, $R_4$, $R_5$ or $R_6$ represents:

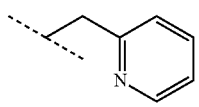

According to an embodiment, in the formulae (I), (II), (III), (IV), (V) or (VI), q is an integer comprised from 0 to 10, preferably from 0 to 5, and more preferably from 1 to 2. In particular, q is 1.

According to an embodiment, in the formulae (I), (II), (III), (IV), (V) or (VI), p is an integer comprised from 0 to 10, preferably from 0 to 5, and more preferably from 1 to 2. In particular, p is 1.

According to an embodiment, in the formulae (I), (II), (III), (IV), (V) or (VI), $R_4$, $R_5$ or $R_6$ represents an alkyl group linear or branched comprising from 1 to 10 carbon atoms, preferably from 1 to 6 carbon atoms.

According to an embodiment, in the formulae (I), (II), (III), (IV), (V) or (VI), $R_4$ and $R_5$ form together, with the nitrogen atoms carrying them, a heterocycle group comprising from 4 to 20 atoms, said heterocycle group optionally comprising at least one heteroatom chosen from O, N and S. In particular, $R_4$ and $R_5$ form together, with the nitrogen atoms carrying them, a heterocycle group comprising from 6 to 10 atoms, and more preferably comprising 6 atoms (including the two nitrogen atoms carrying $R_4$ and $R_5$).

According to an embodiment, in the formulae (I), (II), (III), (IV), (V) or (VI), $R_4$ and $R_5$ form together, with the nitrogen atoms carrying them, a heterocycle group comprising from 9 to 40 atoms, said heterocycle group optionally comprising at least one heteroatom chosen from O, N and S. In particular, $R_4$ and $R_6$ form together, with the nitrogen atoms carrying them, a heterocycle group comprising from 9 to 20 atoms.

According to an embodiment, in the formulae (I), (II), (IV), $B_1$, $B_2$ and $B_4$ are identical.

According to an embodiment, in the formulae (I), (II), (IV), $B_1$, $B_2$ and $B_4$ are different.

According to an embodiment, in the formulae (I), (II), (IV), $B_1$, $B_2$ or $B_4$ represents an alkylene group comprising from 2 to 10 carbon atoms, preferably from 2 to 5, and more preferably from 2 to 3 carbon atoms, said alkylene group being linear or branched.

According to an embodiment, in the formula (I), t is an integer comprised from 0 to 10, preferably from 0 to 5. In particular, t is 0. In particular, t is 1.

According to an embodiment, in the formulae (I) or (II), s is an integer comprised from 0 to 10, preferably from 1 to 5. In particular, s is 1, 2 or 3.

According to an embodiment, in the formulae (I), (II) or (III), r is an integer comprised from 0 to 10, preferably from 1 to 5. In particular, r is 1, 2 or 3, and more preferably r is 2.

According to an embodiment, in the formulae (I), (II) or (III), $R_7$ is H.

According to an embodiment, in the formulae (I), (II) or (III) above-mentioned, $R_7$ is —$(CH_2)_p$COOR', R' representing H, an alkyl group linear or branched comprising from 1 to 10 carbon atoms, or an aryl group comprising from 6 to 20 carbon atoms. In particular, R' represents H. In particular, R' represents an alkyl group linear or branched comprising from 1 to 10 carbon atoms, more preferably from 1 to 4 carbon atoms such as —$C(CH_3)_3$.

According to an embodiment, in the formulae (I), (II) or (III) above-mentioned, $R_7$ represents —$(CH_2)_q$Ar, Ar representing an aryl group comprising from 6 to 20 carbon atoms. In particular, Ar is a phenyl group. In particular, $R_7$ represents —$CH_2$Ph, with Ph representing a phenyl group.

According to an embodiment, in the formulae (I), (II) or (III), above-mentioned, $R_7$ represents —$(CH_2)_q$Het, Het being a heteroaryl group comprising from 6 to 20 atoms, preferably comprising 6 atoms. In particular, $R_7$ represents:

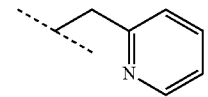

According to an embodiment, in the formulae (I), (II) or (III), $R_7$ represents an alkyl group linear or branched comprising from 1 to 10 carbon atoms, preferably from 1 to 6 carbon atoms.

According to an embodiment, in the formula (I), $B_3$ is:

$$—(CH_2)_2—N(R_7)—(CH_2)_2—,$$

$R_7$ being as defined above.

In particular, in the formula (I), $B_3$ is:

$$—(CH_2)_2—\underset{H}{N}—(CH_2)_2—$$

According to an embodiment, in the formulae (I), (II), (III), (IV), (V) or (VI), Y represents an alkylene group comprising from 1 to 10 carbon atoms, preferably from 1 to 6, and more preferably from 2 to 5 carbon atoms. In particular, Y represents a propylene group.

According to an embodiment, in the formulae (I), (II), (III), (IV), (V) or (VI), $R_1$, $R_2$ and $R_3$ are identical.

According to an embodiment, in the formulae (I), (II), (III), (IV), (V) or (VI), $R_1$, $R_2$ and $R_3$ are different.

According to an embodiment, in the formulae (I), (II), (III), (IV), (V) or (VI), $R_1$, $R_2$ and $R_3$ represent, independently of each other, an alkyl group, linear or branched, comprising from 1 to 10 carbon atoms. In particular, $R_1$ represents an ethyl group. In particular, $R_2$ represents an ethyl group. In particular, $R_3$ represents an ethyl group.

According to an embodiment, in the formulae (I), (II), (III), (IV), (V) or (VI), $R_1$, $R_2$ and $R_3$ represent, independently of each other, an aryl group comprising from 6 to 20 carbon atoms.

According to an embodiment, in the formulae (I), (II), (III), (IV), (V) or (VI), $R_1$, $R_2$ and $R_3$ together with the nitrogen atom carrying them, form a saturated or unsaturated nitrogen-containing heterocycle, said heterocycle being optionally substituted, chosen from the group consisting of: pyrrolidine, imidazolidine, pyrazolidine, piperidine, piperazine, morpholine, pyrrole, pyrazole, imidazole, pyridine, pyrimidine, pyrazine.

According to an embodiment, in the formulae (I), (II), (III), (IV), (V) or (VI), u is 2.

According to an embodiment, in the formula (I), n represents an integer comprised from 1 to 6, preferably from 1 to 4. In particular, n is 3.

According to an embodiment, in the formulae (I), (II), (III), (IV), (V) or (VI), m represents an integer comprised from 1 to 3. In particular, m is 1.

By "total charge" of the compound of formula (I), it is means in the present invention, the "overall charge" of the compound of formula (I). Such compounds are neutral or also called uncharged compounds. The same applies for compounds of formula (II), (III), (IV), (V) or (VI).

According to the invention, X' is an anion. In particular, X' is a conjugate base of an organic or an inorganic acid.

According to an embodiment, the inorganic acid is chosen from the group consisting in: sulfuric acid, hydrochloric acid, phosphoric acid. In particular, the inorganic acid is hydrochloric acid.

According to an embodiment, the organic acid is chosen from the group consisting in: citric acid, acetic acid, formic acid, benzoic acid, salicylic acid, oxalic acid, glycolic acid, lactic acid, glutaric acid and sulfonic acid.

According to an embodiment, X represents a halogen, in particular X represents Cl.

According to an embodiment, $X^{m-}$ is $Cl^-$.

Among the compounds of formula (V), the preferred compounds are:

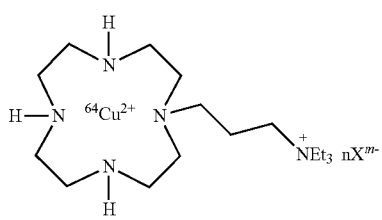
(Va)

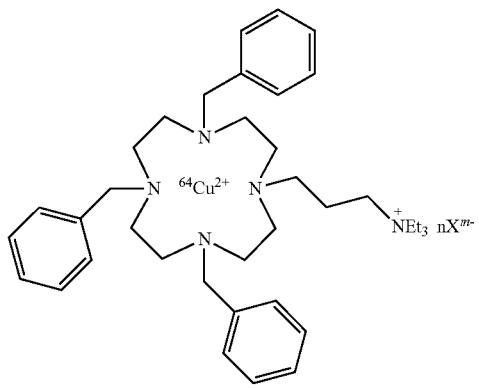
(Vb)

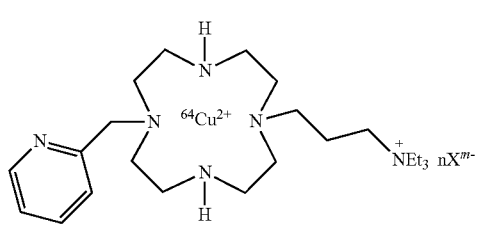
(Vc)

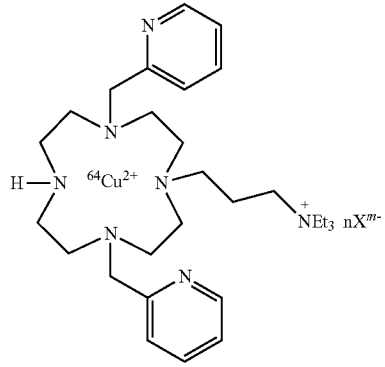
(Vd)

wherein $nX^{m-}$ is as defined above, and in particular $X^{m-}$ is selected from chloride ions, citrate ions and mixtures thereof. In particular, $nX^{m-}$ is $3Cl^-$ or $C_6H_5O_7^{3-}$.

Among the compounds of formula (VI), the preferred compounds are:

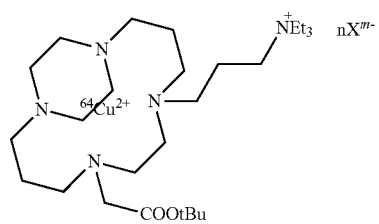
(VIa)

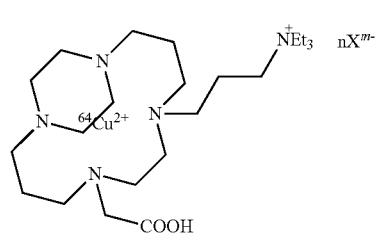
(VIb)

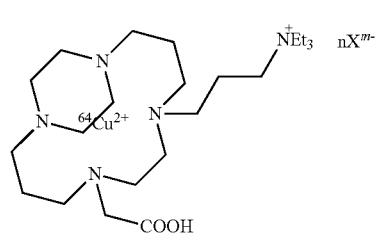
(VIc)

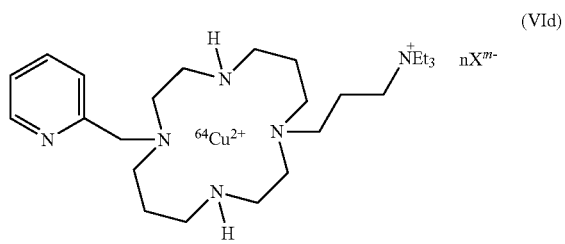
(VId)

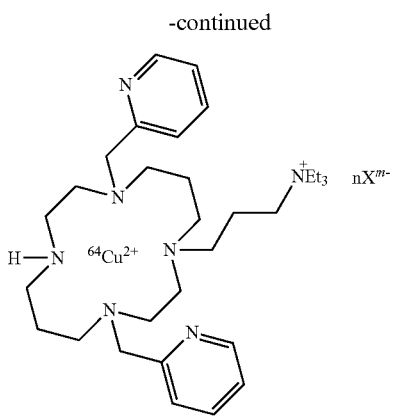
(VIe)

According to an embodiment, among the compounds of formula (I), the preferred compounds are chosen in the group constituting of the following cationic complexes:
[$^{64}$Cu]—N,N,N-Triethyl-3-(1,4,7,10,13-pentaazacyclopentadecan-1-yl)propan-1-aminium copper(II);
[$^{64}$Cu]—N,N,N-Triethyl-3-(1,4,8,11-tetraazacyclotetradecan-1-yl)propan-1-aminium copper(II);
[$^{64}$Cu]—N,N,N-Triethyl-3-(1,4,7,10-tetraazacyclododecan-1-yl)propan-1-aminium copper(II);
[$^{64}$Cu]-3-(8-(2-tert-Butoxy-2-oxoethyl)-1,5,8,12-tetraazabicyclo[10.2.2]hexadecan-5-yl)-N,N,N-triethylpropan-1-aminium copper(II);
[$^{64}$Cu]-3-(8-(Carboxymethyl)-1,5,8,12-tetraazabicyclo[10.2.2]hexadecan-5-yl)-N,N,N-triethylpropan-1-aminium copper(II);
[$^{64}$Cu]—N,N,N-Triethyl-3-(4,7,10-tribenzyl-1,4,7,10-tetraazacyclododecan-1-yl)propan-1-aminium copper(II);
[$^{64}$Cu]—N,N,N-Triethyl-3-(7-(pyridin-2-ylmethyl)-1,4,7,10-tetraazacyclododecan-1-yl)propan-1-aminium copper(II);
[$^{64}$Cu]-3-(4,10-Bis(pyridin-2-ylmethyl)-1,4,7,10-tetraazacyclododecan-1-yl)-N,N,N-triethylpropan-1-aminium copper(II);
[$^{64}$Cu]—N,N,N-Triethyl-3-(8-(pyridin-2-ylmethyl)-1,4,8,11-tetraazacyclotetradecan-1-yl)propan-1-aminium copper(II);
[$^{64}$Cu]-3-(4,11-Bis(pyridin-2-ylmethyl)-1,4,8,11-tetraazacyclotetradecan-1-yl)-N,N,N-triethylpropan-1-aminium copper(II);
associated with encountered anions nX$^{m-}$ wherein nX$^{m-}$ is as defined above, and in particular X$^{m-}$ is selected from chloride ions, citrate ions and mixtures thereof, or their pharmaceutically acceptable salts, such as the hydrochloride salts.

[Definitions]

The term "alkyl" (or "Alk") means a saturated or unsaturated aliphatic hydrocarbon group which may be straight or branched having 1 to 24 carbon atoms in the chain. Preferred alkyl groups have 1 to 6 carbon atoms in the chain. For example, the alkyl group is a methyl, a propyl, a butyl, a tertiobutyl, a pentyl or an isopropyl.

The term "alkylene" means a divalent saturated aliphatic hydrocarbon radical, which may be linear or branched, having from 1 to 24 carbon atoms in the chain.

The term "alkoxy" refers to an —O-alkyl radical.

The term "aryl" refers to an aromatic monocyclic or bicyclic hydrocarbon ring system having 6 to 20 carbons, wherein any ring atom capable of substitution may be substituted by a substituent. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group (possibly substituted). Examples of "arylalkyl" or "aralkyl" include benzyl.

The term "cycloalkyl" as employed herein includes saturated cyclic, bicyclic, tricyclic, or polycyclic hydrocarbon groups having 5 to 20 carbons, wherein any ring atom capable of substitution may be substituted by a substituent. Examples of cycloalkyl moieties include, but are not limited to, cyclohexyl and cycloheptyl.

The term "halo" (or "Hal") refers to the atoms of the group 17 of the periodic table (halogens) and includes in particular fluorine, chlorine, bromine, and iodine atom.

The term "heterocycle" refers to a nonaromatic 3-40 membered monocyclic, 7-40 membered bicyclic, having 1-3 heteroatoms if monocyclic, 1-6 heteroatoms if bicyclic, said heteroatoms selected from O, N, or S (e.g., carbon atoms and 1-3 or 1-6 heteroatoms of N, O, or S if monocyclic or bicyclic, respectively), wherein any ring atom capable of substitution may be substituted by a substituent. Some examples of heterocycle are pyrrolidine, imidazolidine, pyrazolidine, piperidine, piperazine, morpholine, pyrrole, pyrazole, imidazole, pyridine, pyrimidine or pyrazine.

The term "heteroaryl" refers to an aromatic 5-8 membered monocyclic, 8-12 membered bicyclic, having 1-3 heteroatoms if monocyclic, 1-6 heteroatoms if bicyclic, said heteroatoms selected from O, N, or S (e.g., carbon atoms and 1-3 or 1-6 heteroatoms of N, O, or S if monocyclic or bicyclic, respectively), wherein any ring atom capable of substitution may be substituted by a substituent. As example of heteroaryl, mention may be made of pyridine.

The term "substituents" refers to a group "substituted" on an alkyl, cycloalkyl, heterocyclyl, aryl, aralkyl or heteroaryl group at any atom of that group. Suitable substituents include, without limitation, alkyl, alkenyl, alkynyl, alkoxy, halo, hydroxy, cyano, nitro, amino, SO$_3$H, sulphate, phosphate, perfluoroalkyl, perfluoroalkoxy, methylenedioxy, ethylenedioxy, carboxyl, oxo, thioxo, imino (alkyl, aryl, aralkyl), S(O)$_n$ alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl.

As used herein, the term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in Remington's Pharmaceutical Sciences, 19th Edition, Mack Publishing Co., Easton, Pa.

1995. In the case of agents that are solids, it is understood by those skilled in the art that the inventive compounds, agents and salts may exist in different crystalline or polymorphic forms, all of which are intended to be within the scope of the present invention and specified formulae.

As used herein, "pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable vehicle" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein, the compounds of formula (I) are also called "complexes", "macrocyclic complexes", "polyazamacrocycles", "radiotracers", "radiomarkers", "radiolabelled compounds".

As used herein, the compounds of formulae (I'a), (I'b), (I'c), (I'd), (I'e), (I'f), (I'g), (I'h) and (I'i) are called "intermediates", "bifunctional chelator", "ligands". Such compounds are intermediate compounds for the preparation of the compounds of formula (I).

The present invention also concerns a solution comprising a compound of formula (I) as defined above, their pharmaceutically acceptable salts, or their mixtures thereof.

In particular, the solution is an aqueous solution.

According to an embodiment, the solution comprises a mixture of a compound of formula (I) and their pharmaceutical acceptable salts, such as their hydrochloride salts.

According to the invention, the pharmaceutically acceptable salts of the compound of formula (I) are such that the $^{64}$Cu is always chelated in said compound.

In the above solution, the compound of formula (I) may be a compound of formula (II), (III), (IV), (V) or (VI).

The present invention also relates to the process of preparation of the compound of formula (I) as defined above, comprising reacting a compound of formula (I'):

$$(I')$$

with $^{64}$Cu in solution, wherein:
R$_1$, R$_2$, R$_3$, R$_4$, R$_5$, R$_6$, Y, X, B$_1$, B$_2$, B$_3$ and B$_4$ are as defined above; and
n' represents an integer comprised from 0 to 6, preferably from 1 to 4;
m' represents an integer comprised from 1 to 3.

According to an embodiment, the process comprises reacting a compound of formula (I) with $^{64}$Cu in aqueous solution.

According to an embodiment, the process of the invention comprises reacting:
a compound of formula (I') in aqueous solution;
a sodium citrate solution (0.1M) having a pH=6; and
[$^{64}$Cu]Cl$_2$ in an aqueous solution of hydrochloride acid (0.1 M).

Preferably, the compound of formula (I') is first dissolved in water, more particularly in ultrapure water, and then mixed with a sodium citrate solution (0.1 M) having pH=6.

The present invention also concerns a solution susceptible to be obtained according to the process above-mentioned.

In particular, said solution comprises a compound of formula (I), optionally mixed with at least one of its pharmaceutically acceptable salts, such as its hydrochloride salts.

The present also concerns the intermediates compounds of formula (I'), which are in particular chosen in the group consisting of:

(I'a)

(I'b)

(I'c)

(I'd)

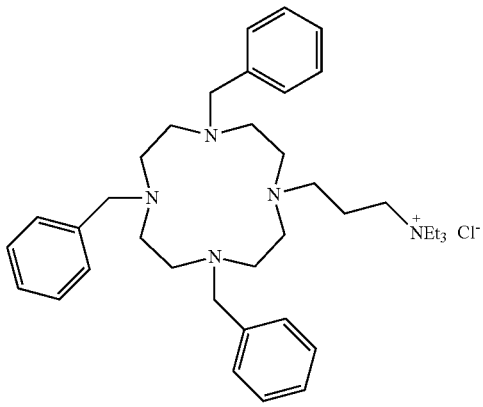
(I'e)

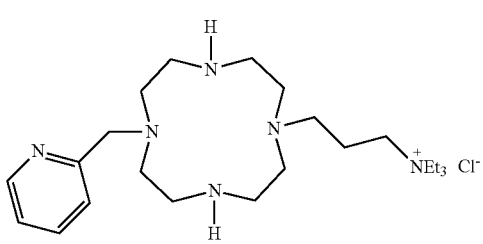
(I'f)

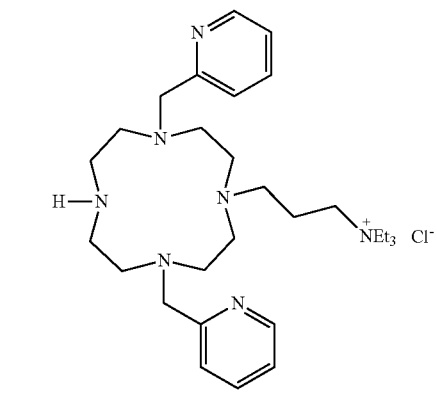
(I'g)

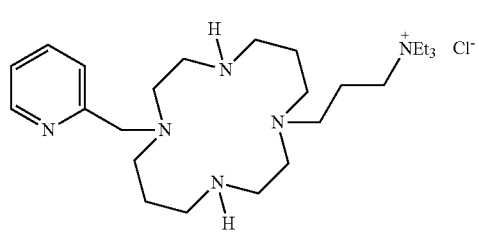
(I'h)

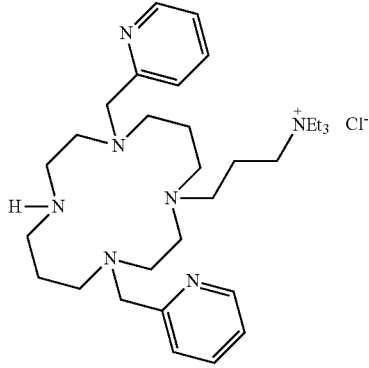
(I'i)

or their pharmaceutically acceptable salts thereof, such as their hydrochloride salts.

In particular, the hydrochloride salts of compounds of formulae (I'a), (I'b), (I'd), (I'e), (I'f), (I'g), (I'h) and (I'i), are tetrachloride salts.

In particular, compounds of formulae (I'a) and (I'd) are in the form of their tetrachloride salts.

The present invention also concerns the process of preparation of a compound of formula (I'a), said process comprising:
  protecting three of the four amino functions of cyclam with a protective group, such as a Boc group;
  carrying out a N-alkylation reaction on the free amino function, in presence of an alkylating agent and a base;
  deprotecting the three protective amino functions preferably with an acidic solution.

The present invention also concerns the process of preparation of a compound of formula (I'b), said process comprising:
  protecting three of the four amino functions of cyclen with a protective group, such as a Boc group;
  carrying out a N-alkylation reaction on the free amino function, in presence of an alkylating agent (such as Br(CH$_2$)$_3$Br$^-$) and a base (such as Na$_2$CO$_3$);
  carrying out a substitution reaction with a compound comprising an amine, such as triethylamine;
  deprotecting the three protective amino functions preferably with an is acidic solution.

The present invention also concerns the process of preparation of a compound of formula (I'c), said process comprising:
  i) reacting cyclam with glyoxal in alcohol solution;
  ii) carrying out a N-alkylation of the compound resulting from step i), with an alkylating agent;
  iii) reacting the compound from step ii) with NaBH$_4$ in alcohol solution;
  iv) carrying out a N-alkylation reaction on the free amino function, in presence of an alkylating agent (such as Br(CH$_2$)$_3$N$^+$Et$_3$, Br$^-$) and a base (such as K$_2$CO$_3$).

The present invention also concerns the process of preparation of a compound of formula (I'd), said process comprising reacting the compound of formula (I'c) with an inorganic acid, such as HCl.

The present invention also concerns the process of preparation of a compound of formula (I'e), said process comprising:
  protecting three of the four amino functions of cyclen with a protective group, such as a benzyl group;

carrying out a N-alkylation reaction on the free amino function, in presence of an alkylating agent and a base.

The present invention also concerns the process of preparation of a compound of formula (I'f), said process comprising:

i) reacting cyclen with glyoxal in alcohol solution, such as in MeOH;

ii) carrying out an N-alkylation of the compound resulting from step i), with an alkylating agent;

iii) reacting the compound from step ii) with $NH_2NH_2$ in aqueous solution;

iv) carrying out a N-alkylation of the compound resulting from step iii), in presence of an alkylating agent (such as $Br(CH_2)_3N^+Et_3$, $Br^-$) and a base (such as $K_2CO_3$), in an amount such that only one of the free amino function reacts.

The present invention also concerns the process of preparation of a compound of formula (I'g), said process comprising:

i) protecting two of the four amino functions of cyclen with a protective group, such as a Cbz;

ii) carrying out a N-alkylation of the compound resulting from step i), with an alkylating agent in an amount adequate to carry out the reaction on the two free amino functions;

iii) deprotecting the two protected amino function by hydrogenation;

iv) carrying out a N-alkylation of the compound resulting from step iii), in presence of an alkylating agent (such as $Br(CH_2)_3N^+Et_3$, $Br^-$) in an amount such that only one of the free amino function reacts.

The present invention also concerns the process of preparation of a compound of formula (I'h), said process comprising:

i) reacting cyclam with glyoxal in alcohol solution, such as in MeOH;

ii) carrying out a N-alkylation of the compound resulting from step i), with an alkylating agent;

iii) reacting the compound from step ii) with $NH_2NH_2$ in aqueous solution;

iv) carrying out a N-alkylation in presence of an alkylating agent (such as $Br(CH_2)_3N^+Et_3$, $Br^-$) and a base (such as $K_2CO_3$), in an amount such that only one of the free amino function reacts.

The present invention also concerns the process of preparation of a compound of formula (I'i), said process comprising:

i) reacting cyclam with a solution of $CH_2O$;

ii) carrying out a N-alkylation of the compound resulting from step i), with an alkylating agent;

iii) carrying out a N-alkylation of the compound resulting from step ii), in presence of an alkylating agent (such as $Br(CH_2)_3N^+Et_3$, $Br^-$) and a base (such as $K_2CO_3$), in an amount such that only one of the free amino function reacts.

According to an embodiment, the compounds of formulae (I'a), (I'b), (I'd), (I'e), (I'f), (I'g), (I'h) and (I'i), may be transformed into their hydrochloride salts by acidification with HCl. In particular, such compounds are dissolved in acidic solution.

The present invention also concerns a kit comprising:

a) a compound of formula (I'):

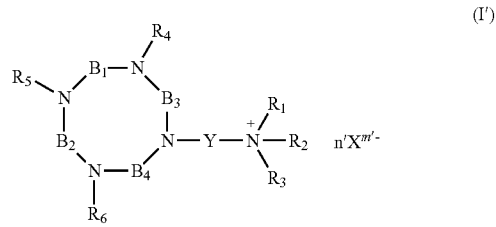

or their pharmaceutical acceptable salts, $R_1$, $R_2$, $R_3$, $R_4$, $R_5$, $R_6$, Y, X, n', m' $B_1$, $B_2$, $B_3$ and $B_4$ being as defined above, and b) a buffer solution pH=6 (0.1 M)

c) $^{64}Cu$ in solution.

In particular, the kit allows the formation of compound of formula (I) by mixing component a), b) and c).

In one embodiment, in the kit of the invention, the compound of formula (I') or its pharmaceutically acceptable salt, is in aqueous solution.

In one embodiment, in the kit of the invention, the buffer solution is a buffer aqueous solution.

In one embodiment, in the kit of the invention, $^{64}Cu$ is in the form of $[^{64}Cu]CuCl_2$ in an aqueous solution, in particular in of hydrochloride acid solution (0.1 M).

The present invention also concerns pharmaceutical compositions comprising as active principle, a compound of formula (I), (II), (III), (IV), (V) or (VI), and a pharmaceutically acceptable vehicle or excipient.

The present invention also relates to a compound of formula (I), (II), (III), (IV), (V) or (VI), or one of its pharmaceutically acceptable salts, for use as a diagnostic agent in PET imaging, in particular in PET-CT imaging.

The present invention also concerns a solution comprising a compound of formula (I) as defined above, their pharmaceutically acceptable salts, or their mixtures thereof, for use as a diagnostic agent in PET imaging, in particular in PET-CT imaging.

Such diagnostic agent may be used for the diagnosis and/or the therapeutic follow-up and/or the treatment of diseases associated with the deregulation of the proteoglycan concentration.

The solution or the pharmaceutical composition abovementioned for PET imaging may be administered by conventional parenteral means such as i.v. administration, and the dosage thereof is determined depending on a radioactivity level at which imaging is considered possible, in view for example of the age and body weight of a patient.

According to an embodiment, the diseases associated with the deregulation of the proteoglycan concentration are selected from the group consisting in: osteoarthritis, arthritis, chondrosarcoma, aneurism, aortic dissection, intervertebral discs degeneration.

Similar compounds of the compounds of formula (I) may also be prepared with other copper isotopes, such as $^{67}Cu$. Such compounds may be obtained by reacting compounds of formula (I') according to the invention, with a solution comprising $^{67}Cu$. Such compounds may have for example the following formula:

$$R_5 \diagdown_{N}^{B_1-N} \diagup^{R_4}_{B_3} \diagdown_{R_1}^{R_1}$$
$$\begin{array}{c} | \\ B_2 \\ \diagdown N-B_4 \\ | \\ R_6 \end{array} \begin{array}{c} {}^{67}Cu^{u+} \\ | \\ N-Y-N-R_2 \quad nX^{m-} \\ | \\ R_3 \end{array}$$

wherein $R_1$, $R_2$, $R_3$, $R_4$, $R_5$, $R_6$, $R_7$, $B_1$, $B_2$, $B_3$, $B_4$, Y, n, X, m and u are as defined in claim 1, Typically, compounds of formula (I) with $^{67}Cu$ instead of $^{64}Cu$ may be used in therapy.

The invention is described in the foregoing by way of non-limiting examples.

FIGURES

EXAMPLES

Figure 1:
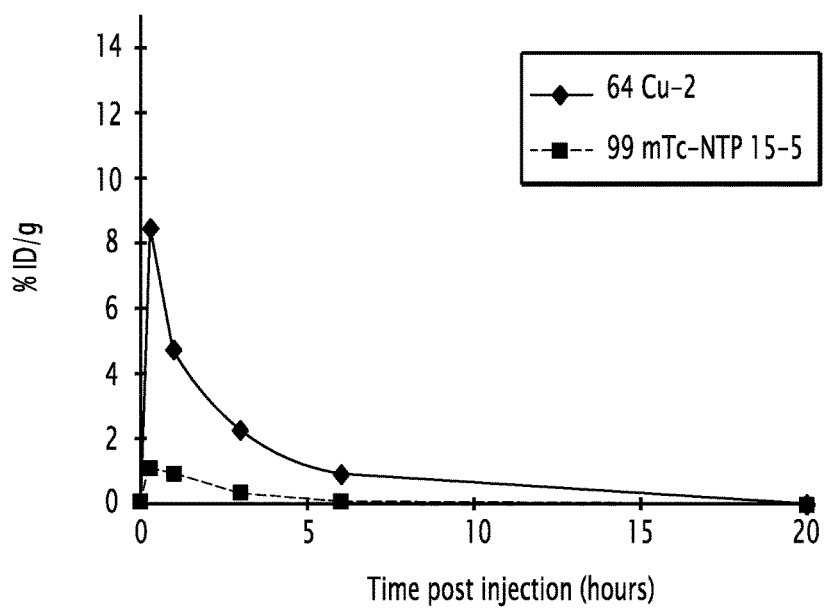
FIG. 1 represents the comparison of the cartilage accumulation of $^{64}Cu$-2 and $^{99m}Tc$-NTP 15-5 in healthy rabbits. It describes the percentage of ID/g of organ for each compound in function of the time post i.v. injection (in hours).

A high-performance liquid chromatography instrument equipped with an evaporative light scattering detector (HPLC-ELSD) was used to assess the chemical purity of intermediates before radiolabelling. The following conditions were used:

column: 4.6×150 mm, 5 µm, Discovery C18 (Supelco Analytical);
flow rate: 0.5 to 1 mL·min$^{-1}$;
column temperature: room temperature;
evaporation chamber temperature: 60° C.;
injected volume from 10 to 50 µL of 1 mM of ligand solution in water (or water/ethanol for poor hydrophilic ligand); mobile phases: solvent A: 20 mM heptafluorobutanoic acid (HFBA) in water, solvent B: 20 mM HFBA in ethanol or acetonitrile (preferably ethanol), A/B ratio is between 80/20 and 20/80 depending on studied ligands. HPLC analysis can be performed in isocratic or gradient elution mode.

Melting points were determined on an Electrothermal IA9100 (capillary) apparatus. NMR spectra 500, 400 or 200 MHz for $^1H$ and 125, 100 or 50 MHz for $^{13}C$ were recorded on Bruker Avance instruments using CDCl$_3$ or D$_2$O as solvents. Chemical shifts were referenced to the residual CDCl$_3$ signals at 7.26 ppm ($^1H$ NMR) and 77.16 ppm ($^{13}C$ NMR) or sodium 3-(trimethylsilyl)propionate-2,2,3,3-d4 respectively.

Electrospray ionization mass spectra (ESI-MS) were obtained on an Esquire-LC instrument (Bruker Daltonics, Wissenbourg, France). The samples were analyzed in methanol in positive mode at final concentration comprised between 1.0 and 10.0 pmol·µL$^{-1}$. ESI-MS spectra were recorded by averaging of 10 spectra.

All the starting materials required for the synthesis of ligands compounds are available from commercial sources. Cyclen and cyclam were purchased from Chematech (France), a compagny specialized in the design and synthesis of polyazamacrocycles. N,N,N-triethyl-3-bromopropan-1-aminium bromide was synthesized according to a slightly modified method described by Botero et al. (Botero M. H. et al., *J. Med. Chem.* 1994, 37, 1439-1445) (see intermediate 1). The 15-5 macrocycle was synthesized according to the general method described by Richman et al. (Richman J. E. et al. *J. Am. Chem. Soc.* 1974, 96, 2268-2270) and detailed by Kovacs et al. (Kovacs Z. et al. *Synth. Commun.* 1999, 29(16), 2817-2822). However the deprotection step of the pentatosylated intermediate 1 has been undertaken according to a cyclen synthesis procedure described by Hettich et al. (Hettich R. et al., *J. Am. Chem. Soc.* 1997, 119, 5638-5647) (see intermediate 2).

It is understood that the man of art will be able to make various modifications without departing from the scope of the invention. In particular, the man of art can use other:

synthetic routes to obtain a compound described hereafter,
protecting groups than those reported in the invention,
purification techniques or methods
radiolabelling procedures.

A. General procedures

Radiolabelling can be performed from both hydrochloride salt or freebase form of the ligands.

Freebase Conversion to Hydrochloride Salt Form

The freebase was converted into the hydrochloride form by treating with hydrogen chloride 2 M in diethyl ether for 1 h at room temperature. After evaporation under vacuum, hydrochloride form was obtained in quantitative yield.

Nota: this procedure is not applicable to compound which decomposes in strong acidic media (i.e. compound 13 described hereafter).

Hydrochloride Salt Conversion to Freebase Form

Hydrochloride form was converted into the freebase by treating with an excess of potassium carbonate in acetone. The resulting suspension was stirred for 1 h at room temperature, filtered to remove solid and evaporated. The residue was diluted in ethanol and passed through a strong anion exchange resin (DOWEX 1×8 chloride form, 200-400 mesh) eluted with ethanol. After evaporation under vacuum, freebase form was obtained in nearly quantitative yield.

Intermediate 1:
N,N,N-Triethyl-3-bromopropan-1-aminium bromide

Anhydrous triethylamine (7.0 mL, 50 mmol) in anhydrous acetone (20 mL) was added dropwise to a solution of dibromopropane (21.19 g, 100 mmol) in anhydrous acetone (20 mL). This mixture was heated for 15 hours at 80° C., cooled to room temperature then the resulting precipitate was filtered, washed with anhydrous acetone (3×15 mL). The crude ammonium was recrystallized in ethanol/diethyl ether solution (9.39 g, 31.0 mmol); m.p.=94-95° C. (Lit. m.p.=90-94° C., Botero M. H. et al., *J. Med. Chem.* 1994, 37, 1439-1445); $^1H$ NMR (400 MHz, D$_2$O) δ 1.30 (t, J=7 Hz, 9H), 2.29 (m, 2H), 3.25-3.39 (m, 8H), 3.56 (t, J=6 Hz, 2H); $^{13}C$ NMR (100 MHz, D$_2$O) δ 7.5 (3C), 25.0 (1C), 30.1 (1C), 53.7 (3C), 56.2 (1C); ESI-MS m/z 222.06 ($^{79}Br$[M$^+$], 100), 224.03 ($^{81}Br$[M$^+$], 98).

Intermediate 2: 1,4,7,10,13-Pentaazacyclopentadecane (15-5)

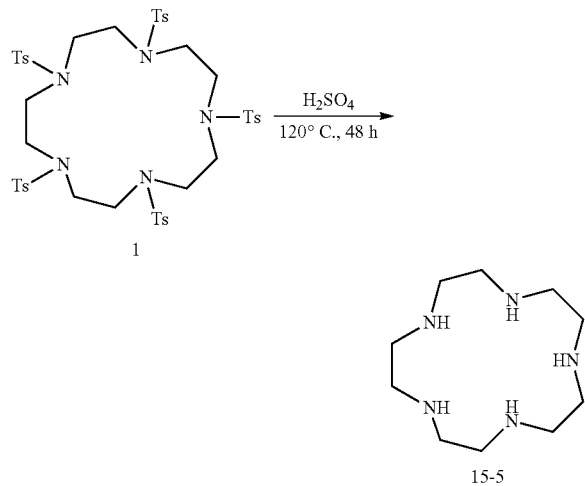

Pentatosylated compound 1 (15.25 g, 15.46 mmol) was dissolved in concentrated sulfuric acid (125 mL). The mixture was stirred at 120° C. for 48 h. After cooling to room temperature, the mixture was added dropwise under vigorous stirring to a solution of methanol/ether (250 mL, 50/50, v/v) at 0° C. The grey precipitate obtained (pentahydrosulfate derivative) was filtered, washed with methanol/ether (3×75 mL, 50/50, v/v) and dried. The solid was then taken up in water (20 mL) and loaded onto an anion exchange resin Amberlyst A26 hydroxide form (Sigma-Aldrich) eluted with water. The basic layers (pH>9) were combined and evaporated under reduced pressure to obtain macrocycle 15-5 as a white solid (3.25 g, 15.09 mmol); $^1$H NMR (400 MHz, CDCl$_3$) δ 1.93 (br s, 5H), 2.70 (s, 20H); $^{13}$C NMR (100 MHz, CDCl$_3$) δ 48.7 (100); ESI-MS m/z 216.10 ([M+H]$^+$, 100).

Example 1: N,N,N-Triethyl-3-(1,4,7,10,13-pentaazacyclopentadecan-1-yl)propan-1-aminium chloride (2)

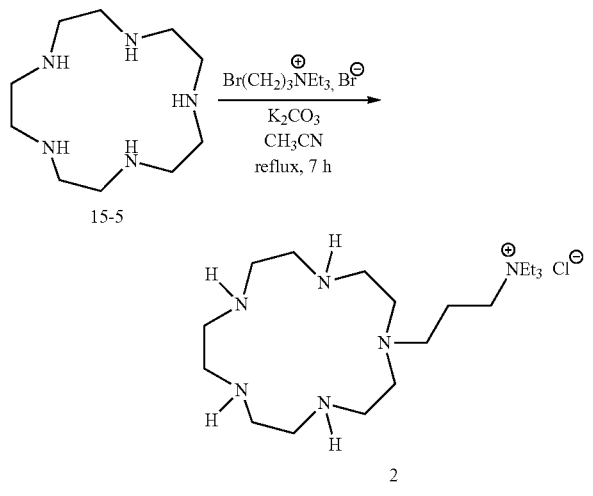

To a solution of macrocycle 15-5 (1.14 g, 5.29 mmol) in anhydrous acetonitrile (35 mL) was added, under argon, potassium carbonate (0.731 g, 5.29 mmol). The suspension was refluxed before slowly adding a solution of N,N,N-triethyl-3-bromopropan-1-aminium bromide (1.12 g, 3.70 mmol) in anhydrous acetonitrile (35 mL) over a period of 1 h under an argon atmosphere. The mixture was refluxed for an additional 7 h. After cooling to room temperature, potassium carbonate excess was removed by filtration. After solvent evaporation, the oily residue was triturated successively with anhydrous toluene (2×40 mL) and diethyl ether (2×40 mL) to remove 15-5 starting material and purified on a C18-reversed-phase silicagel column (40-63 μm, 90 Å). The column was first eluted with a water 20 mM HFBA/acetonitrile 20 mM HFBA solution (80/20, v/v) to remove impurities then with water 20 mM HFBA/acetonitrile 20 mM HFBA (70/30, v/v). The fractions of interest were combined and evaporated under reduced pressure. The oily residue obtained was taken up in acetone (15 mL) and potassium carbonate (3.04 g, 22 mmol) was added. The resulting suspension was stirred for 1 h at room temperature until gas evolution ceased, then filtered to remove solid and evaporated under reduced pressure. The resulting sticky solid was diluted in ethanol (5 mL) and passed through a strong anion exchange resin (DOWEX 1×8 chloride form, 200-400 mesh) eluted with ethanol. After evaporation, 2 was obtained as a white hygroscopic compound (1.10 g, 2.80 mmol); NMR $^1$H (400 MHz, D$_2$O) δ 1.26 (t, 9H, J=8 Hz), 1.91 (quint, 2H, J=8 Hz), 2.72 (t, 2H, J=8 Hz), 2.90 (m, 4H), 3.09 (s, 4H), 3.14 (m, 6H), 3.19 (m, 4H), 3.29 (m, 10H); NMR $^{13}$C (100 MHz, D$_2$O) δ 7.8 (3C), 14.6 (1C), 44.7 (1C), 45.1 (2C), 46.2 (2C), 46.3 (2C), 46.7 (2C), 50.9 (2C), 53.9 (3C), 55.6 (1C); ESI-MS m/z 179.16 ([M+H]$^{2+}$, 100).

Example 2: N,N,N-Triethyl-3-(1,4,8,11-tetraazacyclotetradecan-1-yl)propan-1-aminium chloride hydrochloride salt (5)

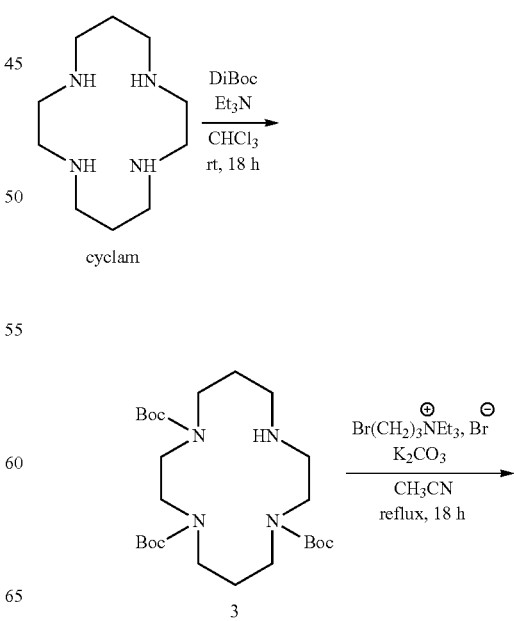

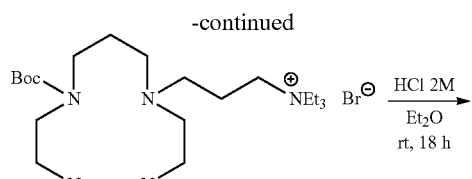

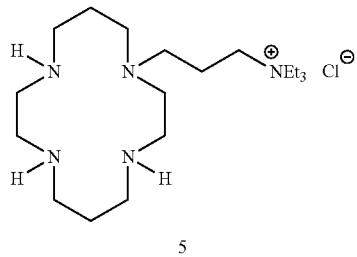

To a solution of cyclam (1.50 g, 7.49 mmol) in chloroform (200 mL) was added a solution of di-tert-butyl dicarbonate (4.90 g, 22.5 mmol) and triethylamine (3.79 g, 37.5 mmol) in chloroform (50 mL). The resulting solution was stirred for 18 h at room temperature and washed with an aqueous potassium carbonate solution (0.5 M, 3×150 mL). The organic layer was dried over sodium sulfate, filtered and evaporated under reduced pressure. The white solid residue was purified by column chromatography on silica gel with ethyl acetate/methanol (97/3, v/v) as eluent to give in order of elution:

- tetra-Boc-protected cyclam ($R_f$=0.85, EtOAc/MeOH, 90/10, SiO$_2$); white solid (0.74 g, 1.24 mmol); m.p.=66-68° C.; NMR $^1$H (400 MHz, CDCl$_3$) δ 1.45 (s, 36H), 1.73 (m, 4H), 3.36 (m, 16H); NMR $^{13}$C (100 MHz, CDCl$_3$) δ 28.6 (14C), 46.8 (4C), 49.3 (4C), 79.9 (4C), 155.8 (4C),
- tri-Boc-protected cyclam 3 ($R_f$=0.36, EtOAc/MeOH, 90/10, SiO$_2$); white solid (2.78 g, 5.54 mmol); m.p.=57-59° C.; NMR $^1$H (500 MHz, CDCl$_3$) δ 1.447 (s, 18H), 1.453 (s, 9H), 1.74 (m, 2H), 1.90 (m, 2H), 2.67 (m, 2H), 2.84 (m, 2H), 3.27-3.42 (m, 12H); NMR $^{13}$C (50 MHz, CDCl$_3$) δ 28.6 (11C), 45.6 (1C), 46.3 (1C), 46.9 (2C), 48.0 (2C), 48.8 (2C), 79.8 (1C), 80.0 (2C), 155.5 (1C), 155.8 (2C); ESI-MS m/z 501.34 ([M+H]$^+$, 100).

To a suspension of compound 3 (2.00 g, 3.99 mmol) and potassium carbonate (0.55 g, 3.99 mmol) in acetonitrile (50 mL) was added a solution of N,N,N-triethyl-3-bromopropan-1-aminium bromide (1.21 g, 3.99 mmol) in acetonitrile (50 mL). The resulting mixture was refluxed overnight under an argon atmosphere. After cooling to room temperature, solid was removed by filtration. After solvent evaporation, the residue was purified by column chromatography on alumina with acetone/ethanol/ammonium hydroxide solution (90/10/1, v/v/v) as eluent to give compound 4 as a white solid (1.04 g, 1.44 mmol); NMR $^1$H (400 MHz, D$_2$O) δ 1.29 (t, 9H, J=7 Hz), 1.47 (s, 27H), 1.74 (m, 2H), 1.86 (m, 4H), 2.60 (m, 4H), 2.72 (m, 2H), 3.18 (m, 2H), 3.33 (m, 18H); NMR $^{13}$C (100 MHz, D$_2$O) δ 7.10, 18.8, 25.9, 28.2, 46.7, 47.2, 48.0, 51.0, 51.8, 53.1, 55.0, 55.2, 62.7, 81.6, 157.4; ESI-MS m/z 643 ([M$^+$], 100).

Compound 4 (0.87 g, 1.20 mmol) was mixed under argon with anhydrous hydrogen chloride 2 M in diethyl ether (10 mL) for 18 h at room temperature. After evaporation under vacuum, the residue was dissolved in deionized water (5 mL) and passed through a strong anion exchange resin (DOWEX 1×8 chloride form, 200-400 mesh) eluted with an aqueous 0.1 M hydrochloric acid solution. After evaporation, 5 was obtained as a white solid (0.60 g, 1.14 mmol); NMR $^1$H (200 MHz, D$_2$O) δ 1.18 (m, 9H), 2.12 (m, 6H), 3.70-3.23 (m, 26H); NMR $^{13}$C (50 MHz, D$_2$O) δ 7.0, 17.7, 18.2, 18.7, 37.0, 37.5, 41.0, 41.5, 45.2, 48.3, 52.3, 53.0, 53.3; ESI-MS m/z 342 ([M$^+$], 100).

Example 3: N,N,N-Triethyl-3-(1,4,7,10-tetraazacyclododecan-1-yl)propan-1-aminium chloride hydrochloride salt (9)

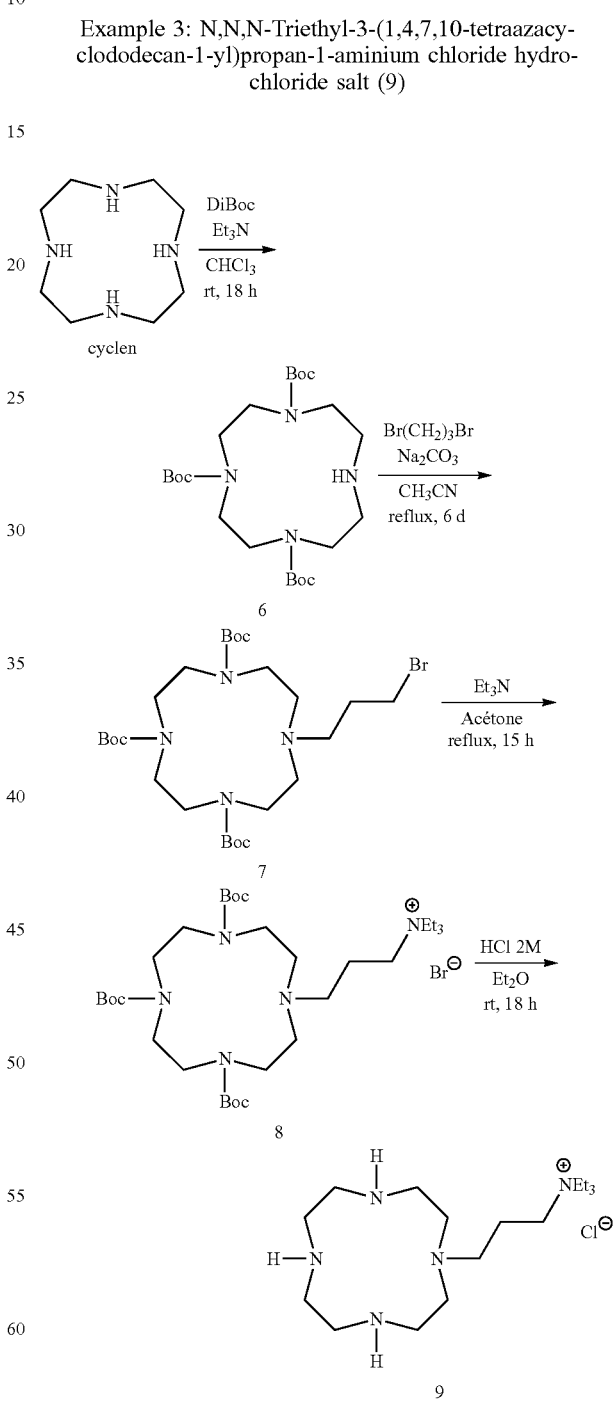

To a solution of cyclen (2.00 g, 11.6 mmol) and triethylamine (3.60 g, 35.6 mmol) in chloroform (60 mL) was added at 0° C. a solution of di-tert-butyl dicarbonate (7.77 g, 35.6 mmol) in chloroform (40 mL). The resulting solution was stirred for 18 h at room temperature and washed with deionized water (2×50 mL). The organic layer was dried over sodium sulfate, filtered and evaporated under reduced pressure. The oily residue was purified by column chromatography on silica gel with diethyl ether as eluent to give in order of elution:

tetra-Boc-protected cyclen ($R_f$=0.69, Et$_2$O, SiO$_2$); white solid (1.46 g, 2.55 mmol); NMR $^1$H (400 MHz, CDCl$_3$) δ 1.46 (s, 36H), 3.38 (br s, 16H); NMR $^{13}$C (100 MHz, CDCl$_3$) δ 28.7, 50.5, 80.1, 156.3, tri-Boc-protected cyclen 6 ($R_f$=0.27, Et$_2$O, SiO$_2$); white solid (3.32 g, 7.02 mmol); NMR $^1$H (400 MHz, CDCl$_3$) δ 1.44 (s, 18H), 1.46 (s, 9H), 2.84 (br s, 4H), 3.28 (br s, 6H), 3.38 (br s, 2H), 3.62 (br s, 4H); NMR $^{13}$C (100 MHz, CDCl$_3$) δ 28.6, 28.8, 49.7, 51.1, 79.4, 79.6, 157.7, To a suspension of sodium carbonate (0.78 g, 7.36 mmol) and 1,3-dibromopropane (2.98 g, 14.8 mmol) in anhydrous acetonitrile (20 mL) was added dropwise under argon a solution of 6 (1.74 g, 3.68 mmol) in anhydrous acetonitrile (20 mL). The resulting mixture was refluxed for 6 d under argon atmosphere. After cooling to room temperature, solid was removed by filtration. After evaporation under vacuum, the oily residue was purified by column chromatography on silica gel eluted with cyclohexane to remove 1,3-dibromopropane excess, and then with diethyl ether to give in order of elution:

7 ($R_f$=0.61, Et$_2$O, SiO$_2$); white solid (1.06 g, 1.79 mmol); NMR $^1$H (500 MHz, CDCl$_3$) δ 1.44 (s, 18H), 1.45 (s, 9H), 2.01 (quint, 2H, J=7 Hz), 2.62 (br s, 2H), 2.69 (br s, 4H), 3.26 (br s, 2H), 3.30 (br s, 4H), 3.38 (t, 2H, J=7 Hz), 3.48 (br s, 4H), 3.54 (br s, 2H); NMR $^{13}$C (125 MHz, CDCl$_3$) δ 27.4, 28.6, 28.8, 32.0, 48.0, 50.3, 50.8, 53.7, 54.8, 79.5, 79.7, 155.5, 155.8, 156.3, starting compound 6 (0.59 g, 1.25 mmol).

To a solution of 7 (1.06 g, 1.79 mmol) in acetone (30 mL) was added triethylamine (0.72 g, 7.12 mmol). The solution was refluxed for 15 h and then cooled to room temperature and evaporated under vacuum to give compound 8 as a white solid (1.06 g, 1.53 mmol); NMR $^1$H (400 MHz, D$_2$O) δ 1.29 (t, 9H, J=7 Hz), 1.45 (s, 18H), 1.48 (s, 9H), 1.84 (br s, 2H), 2.74 (br s, 6H), 3.15 (t, 2H, J=8 Hz), 3.31 (q, 6H, J=7 Hz), 3.39 (br s, 4H), 3.44 (br s, 4H), 3.58 (br s, 4H); NMR $^{13}$C (100 MHz, D$_2$O) δ 6.7, 28.0, 41.8, 46.2, 47.4, 49.1, 52.7, 54.9, 81.3, 157.2, 157.5.

Compound 8 (1.00 g, 1.44 mmol) was mixed with an anhydrous hydrogen chloride 2 M in diethyl ether solution (10 mL) for 18 h at room temperature. After evaporation under vacuum, the white solid was dissolved in deionized water (5 mL) and passed through a strong anion exchange resin (DOWEX 1×8 chloride form, 200-400 mesh) eluted with a 0.1 M aqueous hydrochloric acid solution. After evaporation under vacuum, 9 was obtained as a white solid (0.71 g, 1.43 mmol); NMR $^1$H (400 MHz, D$_2$O) δ 1.29 (t, 9H, J=7 Hz), 1.93 (q, 2H, J=8 Hz), 2.77 (t, 2H, J=8 Hz), 2.96 (m, 8H), 3.18 (m, 10H), 3.32 (q, 6H, J=7 Hz); NMR $^{13}$C (100 MHz, D$_2$O) δ 7.6 (3C), 16.5 (1C), 42.4 (2C), 42.8 (2C), 45.2 (2C), 47.9 (2C), 49.4 (1C), 53.6 (3C), 55.1 (1C); ESI-MS m/z 314.35 ([M$^+$], 70), 157.65 ([M+H]$^{2+}$, 100).

Nota: Freebase form of 9 can be obtained from cyclen in an analogous manner to that described in example 1 for compound 2.

Example 4: 3-(8-(2-tert-Butoxy-2-oxoethyl)-1,5,8,12-tetraazabicyclo[10.2.2]hexadecan-5-yl)-N,N,N-triethylpropan-1-aminium chloride (13)

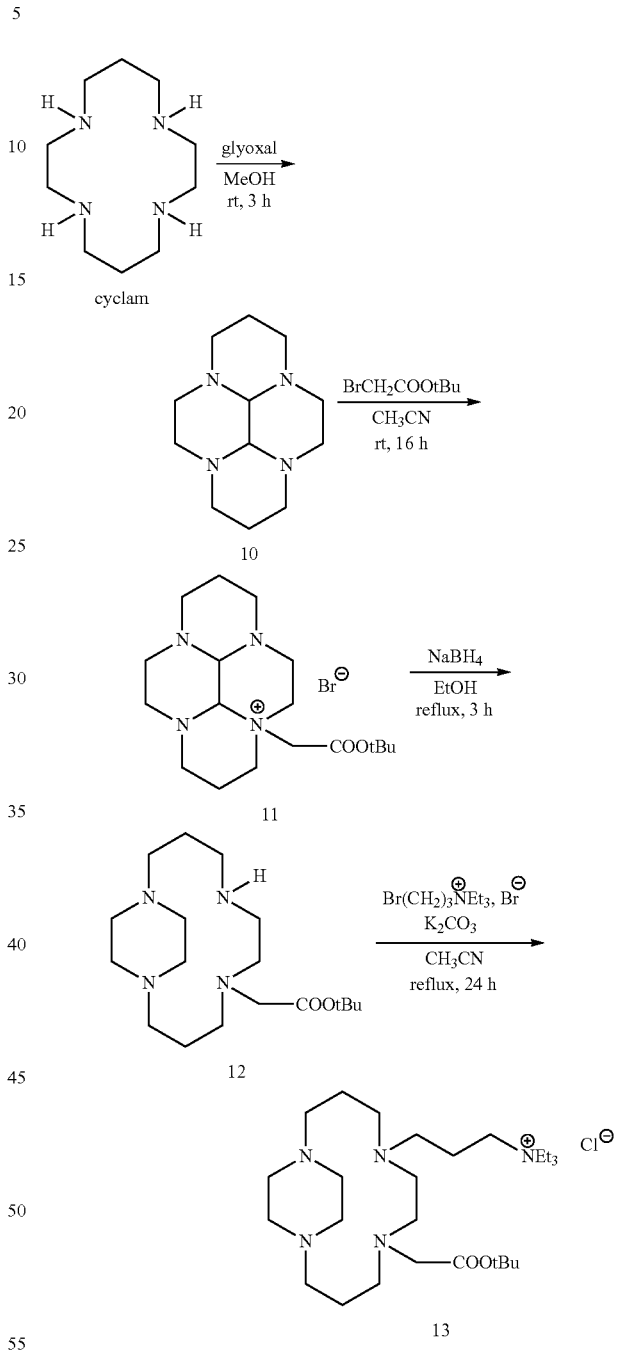

To a solution of glyoxal (9.98 mmol) in methanol (25 mL) cooled to −10-0° C., was added dropwise a solution of cyclam (2.00 g, 9.98 mmol) in methanol (70 mL). The resulting solution was stirred for 3 h at room temperature. After solvent evaporation, the residue was taken up in diethyl ether (50 mL) and stirred overnight at room temperature. The resulting solid was removed by filtration. After evaporation under vacuum, 10 was obtained as a white solid (2.00 g, 9.00 mmol); NMR $^1$H (200 MHz, CDCl$_3$) δ 1.14 (s, 1H), 1.21 (s, 1H), 2.00-2.40 (m, 8H), 2.75 (m, 2H), 2.90 (m, 6H), 3.04 (s, 2H), 3.48 (t, 2H, J=8 Hz); NMR $^{13}$C (50 Hz, CDCl$_3$) δ 19.7, 44.9, 52.5, 54.5, 56.2, 77.1.

To a solution of 10 (0.90 g, 4.06 mmol) in anhydrous acetonitrile (40 mL) was added tert-butylbromoacetate (3.26 g, 16.7 mmol). The reaction solution was stirred for 16 h at room temperature. After solvent evaporation under vacuum, the oily residue was triturated in diethyl ether (150 mL) to afford compound 11 as a white solid (1.65 g, 3.95 mmol); NMR $^1$H (200 MHz, D$_2$O) δ 1.49 (m, 10H), 1.84 (m, 1H), 2.19 (m, 2H), 2.43 (q, 4H, J=13 Hz), 2.96 (m, 7H) 3.50 (m, 2H), 3.76 (m, 1H), 3.91 (m, 3H), 4.34 (d, 2H, J=16 Hz), 4.63 (d, 1H, J=16 Hz); NMR $^{13}$C (50 MHz, D$_2$O) δ 18.5, 19.1, 27.6, 42.4, 46.6, 50.6, 51.8, 52.5, 53.8, 54.2, 58.9, 62.0, 69.9, 83.2, 87.6, 163.7.

To a solution of 11 (0.77 g, 1.84 mmol) in anhydrous ethanol (50 mL) was added sodium borohydride (1.65 g, 43.6 mmol) portionwise at room temperature. The reaction solution was stirred 30 min at room temperature from the last addition and then refluxed for 3 h. After cooling to room temperature, deionized water (30 mL) was added. After evaporation under vacuum, the residue was taken up in deionized water (40 mL). The resulting solution was adjusted to pH 12 with a few droplets of an aqueous solution of potassium hydroxide (10%, m/m) and extracted with dichloromethane (4×50 mL). The combined organic layers were dried over sodium sulfate, filtered and evaporated under reduced pressure to afford compound 12 as a yellow oil (0.59 g, 1.73 mmol); NMR $^1$H (400 MHz, CDCl$_3$) δ 1.42 (s, 9H), 1.61 (quint, 2H, J=5 Hz), 1.71 (quint, 2H, J=5 Hz), 2.17 (dt, 2H, J=10 Hz, 4 Hz), 2.55 (m, 6H), 2.68 (t, 2H, J=5 Hz), 2.84 (m, 6H), 2.95 (t, 2H, J=6 Hz), 3.10 (dt, 2H, J=10 Hz, 4 Hz), 3.27 (s, 2H); NMR $^{13}$C (100 MHz, CDCl$_3$) δ 23.5 (1C), 26.1 (1C), 28.3 (3C), 47.2 (1C), 48.3 (2C), 50.8 (1C), 51.2 (2C), 52.0 (1C), 54.9 (2C), 55.9 (1C), 56.9 (1C), 81.0 (1C), 170.7 (1C).

To a suspension of compound 12 (0.59 g, 1.73 mmol) and potassium carbonate (0.29 g, 2.06 mmol) in anhydrous acetonitrile (30 mL) was added a solution of N,N,N-triethyl-3-bromopropan-1-aminium bromide (0.62 g, 2.06 mmol) in acetonitrile (20 mL). The reaction mixture was refluxed for 24 h under an argon atmosphere. After cooling to room temperature, solid was removed by filtration. After solvent evaporation, the residue was purified by column chromatography on alumina with acetone/ethanol/ammonium hydroxide solution (90/10/1 to 70/30/1, v/v/v) as eluent.

The oily residue was dissolved in ethanol (3 mL) and passed through a strong anion exchange resin (type DOWEX 1×8 chloride form, 200-400 mesh) eluted with ethanol. After solvent evaporation under reduced pressure, 13 was obtained as a slightly brown solid (0.35 g, 0.68 mmol); NMR $^1$H (200 MHz, D$_2$O) δ 1.25 (br s, 9H), 1.45 (s, 9H), 1.78 (m, 4H), 2.21 (m, 2H), 2.72 (m, 12H), 3.34 (m, 16H), 3.73 (m, 2H), 3.94 (m, 2H); NMR $^{13}$C (50 MHz, D$_2$O) δ 7.1, 15.7, 21.3, 24.5, 27.8, 44.5, 46.8, 48.5, 53.1, 53.6, 54.9, 56.5, 59.5, 83.2, 173.6.

Example 5: 3-(8-(Carboxymethyl)-1,5,8,12-tetraazabicyclo[10.2.2]hexadecan-5-yl)-N,N,N-triethylpropan-1-aminium chloride hydrochloride salt (14)

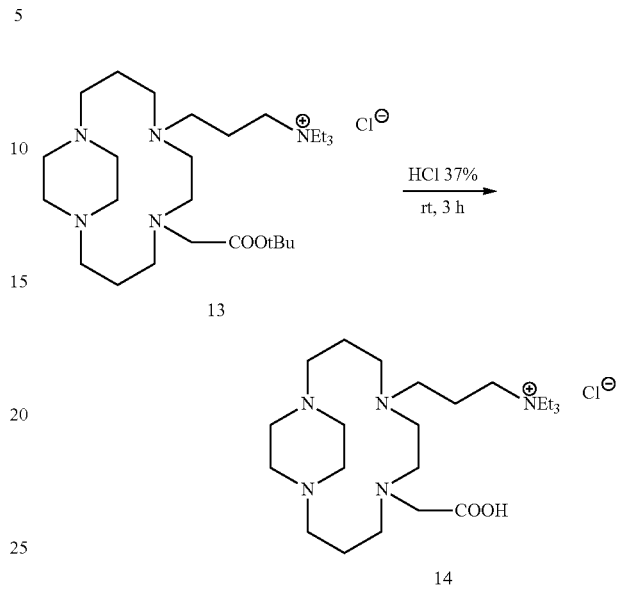

Compound 13 (0.66 g, 1.27 mmol) was stirred with fuming hydrochloric acid (37% in water, 10 mL) at room temperature for 3 h. After evaporation under vacuum, compound 14 was obtained in quantitative yield as a white solid (0.77 g, 1.27 mmol); NMR $^1$H (200 MHz, D$_2$O) δ 1.21 (m, 9H), 1.97 (m, 4H), 2.13 (m, 2H), 2.75 (m, 2H), 3.00 (m, 6H), 3.27 (m, 12H), 3.53 (m, 8H), 3.77 (m, 4H); NMR $^{13}$C (50 MHz, D$_2$O) δ 7.4, 15.9, 21.7, 43.5, 45.0, 45.7, 47.4, 51.2, 53.2, 53.7, 54.0, 54.5, 54.7, 55.0, 55.8, 56.3, 59.3, 60.6, 176.8.

Example 6: N,N,N-Triethyl-3-(4,7,10-tribenzyl-1,4,7,10-tetraazacyclododecan-1-yl)propan-1-aminium chloride (16)

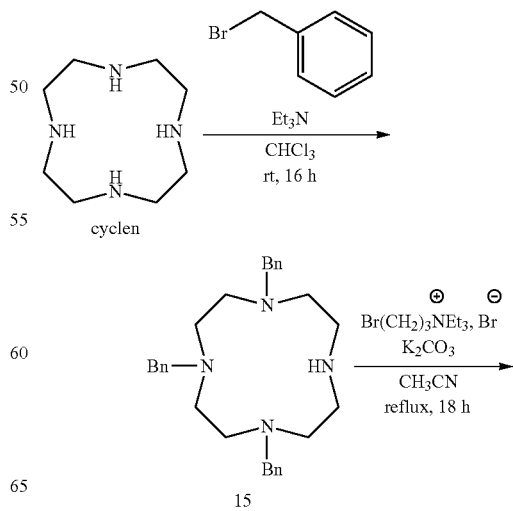

-continued

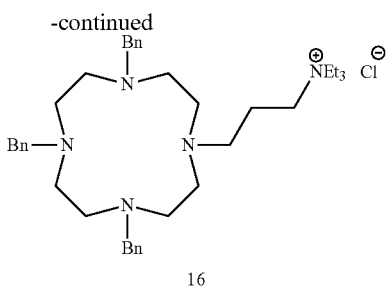

16

To a solution of cyclen (0.50 g, 2.90 mmol) and triethylamine (2.94 g, 29.1 mmol) in chloroform (30 mL) was added dropwise a solution of benzyl bromide (1.74 g, 10.2 mmol) in chloroform (10 mL). The resulting solution was stirred for 16 h at room temperature and washed with deionized water (3×40 mL). The organic layer was dried over sodium sulfate, filtered and evaporated under reduced pressure. The oily residue was purified by column chromatography on alumina with ethyl acetate/methanol solution (98/2 to 95/5, v/v) as eluent to give in order of elution:

tetrabenzyl derivative ($R_f$=0.25, EtOAc/MeOH, 95/5, $Al_2O_3$); white solid (0.32 g, 0.61 mmol); NMR $^1$H (400 MHz, $CDCl_3$) δ 2.69 (s, 16H), 3.43 (s, 8H), 7.24 (m, 12H), 7.36 (dd, 8H, J=7.8 Hz, 1.8 Hz); NMR $^{13}$C (100 MHz, $CDCl_3$) δ 53.1, 60.2, 126.7, 128.2, 129.1, 140.2, compound 15 ($R_f$=0.05, EtOAc/MeOH, 95/5, $Al_2O_3$); white solid (0.62 g, 1.40 mmol); NMR $^1$H (400 MHz, $CDCl_3$) δ 2.53 (s, 8H), 2.64 (m, 4H), 2.72 (m, 4H), 3.27 (s, 2H), 3.53 (s, 4H), 7.20 (m, 11H), 7.36 (dd, 4H, J=7.7 Hz, 1.7 Hz); NMR $^{13}$C (100 MHz, $CDCl_3$) δ 47.6, 51.0, 51.5, 61.3, 126.9, 127.4, 128.2, 128.4, 129.4, 139.2.

To a suspension of compound 15 (0.33 g, 0.74 mmol) and potassium carbonate (0.10 g, 0.74 mmol) in anhydrous acetonitrile (30 mL) was added a solution of N,N,N-triethyl-3-bromopropan-1-aminium bromide (0.23 g, 0.74 mmol) in anhydrous acetonitrile (20 mL). The resulting mixture was refluxed overnight under an argon atmosphere. After cooling to room temperature, solid was removed by filtration and the filtrate was evaporated under reduced pressure. The residue was purified by column chromatography on alumina with dichloromethane/methanol solution (98/2 to 95/5, v/v) as eluent to give in order of elution:

starting compound 15 ($R_f$=0.53, $CH_2Cl_2$/MeOH, 95/5, $Al_2O_3$); (0.046 g, 0.10 mmol), bromide derivative of compound 16 ($R_f$=0.26, $CH_2Cl_2$/MeOH, 95/5, $Al_2O_3$); white solid (0.36 g, 0.54 mmol).

The bromide derivative was taken up in methanol (3 mL) and passed through a strong anion exchange resin (DOWEX 1×8 chloride form, 200-400 mesh) eluted with methanol. After evaporation under vacuum, compound 16 was obtained (0.31 g, 0.50 mmol) as a white solid; NMR $^1$H (500 MHz, $CDCl_3$) δ 1.26 (br s, 9H), 2.23 (br s, 2H), 2.70 (br s, 6H), 2.78 (br s, 4H), 3.12 (br s, 2H), 3.18 (m, 2H), 3.44 (m, 12H), 3.66 (m, 6H), 7.13-7.40 (m, 15H); NMR $^{13}$C (125 MHz, $CDCl_3$) δ 8.1, 20.5, 48.4, 49.0, 49.3, 51.8, 52.0, 53.6, 55.2, 57.3, 60.3, 127.9, 128.2, 128.7, 128.9, 130.5, 131.0, 136.6.

Example 7: N,N,N-Triethyl-3-(7-(pyridin-2-ylmethyl)-1,4,7,10-tetraazacyclododecan-1-yl)propan-1-aminium chloride (20)

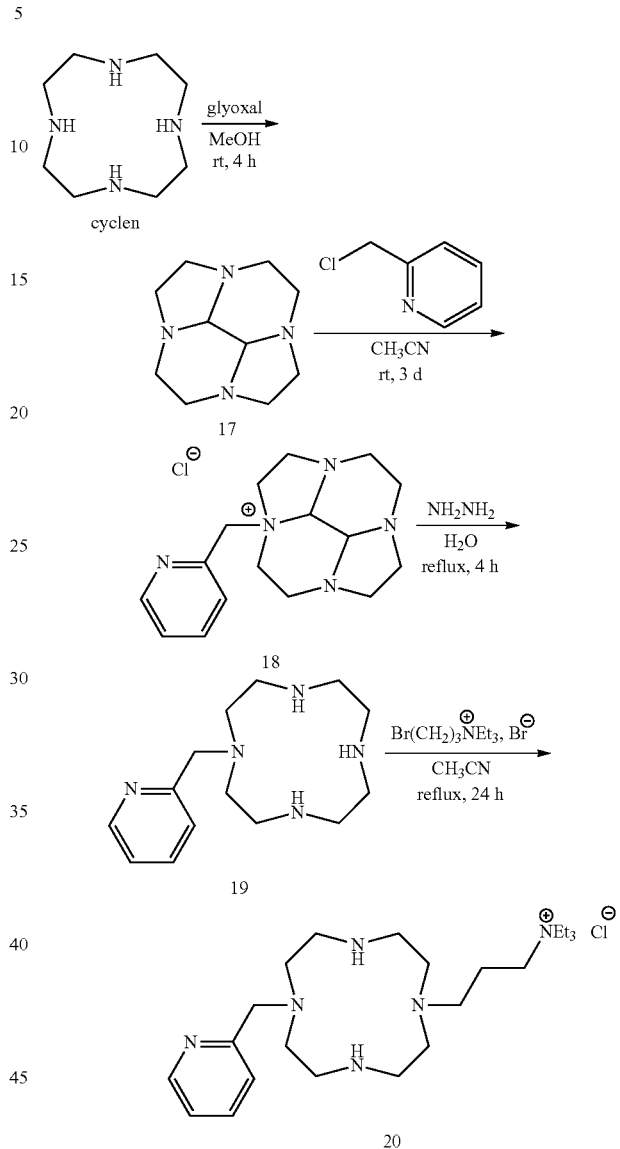

A solution of cyclen (4.00 g, 23.2 mmol) and glyoxal (40% in water, m/m) (2.67 mL, 23.2 mmol) in methanol (20 mL) was stirred for 4 h at room temperature. After solvent evaporation, the residue was taken up in diethyl ether (20 mL) and stirred overnight at room temperature. The resulting solid was removed by filtration and the filtrate was evaporated under vacuum to give compound 17 as a yellow oil (4.30 g, 22.1 mmol); NMR $^1$H (200 MHz, $CDCl_3$) δ 2.64 (m, 8H), 2.97 (m, 8H), 3.16 (s, 2H); NMR $^{13}$C (200 MHz, $CDCl_3$) δ 50.4, 51.2, 77.6; ESI-MS m/z 195.13 ([MH]$^+$, 100).

An aqueous solution of 2-(chloromethyl)pyridine hydrochloride (1.80 g, 11.0 mmol) in 4 M aqueous sodium hydroxide solution (20 mL) was extracted with dichloromethane (3×20 mL). The combined organic layers were dried over sodium sulfate, filtered and evaporated under reduced pressure to afford the unstable 2-(chloromethyl)pyridine. To a solution of this reagent in anhydrous acetonitrile (20 mL) was added a solution of compound 17 (1.13 g, 5.81 mmol) in anhydrous acetonitrile (20 mL). The resulting solution was stirred for 3 d at room temperature under an argon atmosphere. The red precipitate was filtered, washed with anhydrous acetonitrile (20 mL), dried under vacuum to give compound 18 as a pink solid (1.48 g, 4.60 mmol); NMR $^1$H (400 MHz, D$_2$O) δ 2.55 (m, 2H), 2.83 (m, 3H), 2.95 (m, 1H), 3.09 (t, 1H, J=12 Hz), 3.22 (d, 1H, J=12 Hz), 3.25-3.40 (m, 3H), 3.74 (t, 1H, J=8 Hz), 3.62-3.72 (m, 2H), 3.78 (d, 1H, J=2.4 Hz), 3.81 (s, 1H), 4.09 (d, 1H, J=2.4 Hz), 4.40 (td, 1H, J=11.2 Hz, 3.2 Hz), 4.80 (d$_{AB}$, 1H, J=14 Hz), 4.99 (d$_{AB}$, 1H, J=14 Hz), 7.62 (m, 1H), 7.73 (d, 1H, J=8 Hz), 8.02 (td, 1H, J=7.6 Hz, 1.2 Hz), 8.71 (d, 1H, J=4.8 Hz); NMR $^{13}$C (100 MHz, D$_2$O) δ 43.9, 47.6, 47.7, 48.2, 48.3, 51.3, 58.1, 61.8, 62.1, 71.7, 83.2, 125.9, 128.1, 138.9, 147.2, 150.3; ESI-MS m/z 286.17 ([M]$^+$, 100).

A solution of compound 18 (1.20 g, 3.73 mmol) in hydrazine monohydrate (15 mL) was refluxed for 4 h and then cooled to 0° C. overnight. The precipitate was filtered and dried under vacuum to afford compound 19 as a white solid (0.64 g, 2.43 mmol). NMR $^1$H (400 MHz, D$_2$O) δ 2.58-2.63 (m, 12H), 2.75 (m, 4H), 3.74 (s, 2H), 7.36 (t, 1H, J=6 Hz), 7.53 (d, 1H, J=8 Hz), 7.85 (t, 1H, J=8 Hz), 8.45 (d, 1H, J=6 Hz); NMR $^{13}$C (100 MHz, D$_2$O) δ 43.9, 45.0, 45.7, 51.6, 60.4, 123.7, 125.2, 138.7, 148.8, 159.1; ESI-MS m/z 264.16 ([MH]$^+$, 100).

A solution of compound 19 (0.85 g, 3.23 mmol) and N,N,N-triethyl-3-bromopropan-1-aminium bromide (0.98 g, 3.23 mmol) in anhydrous acetonitrile (15 mL) was refluxed for 24 h. After cooling to room temperature and solvent evaporation under reduced pressure, the residue was purified by column chromatography on alumina with dichloromethane/methanol solution (98/2 to 95/5, v/v) as eluent to afford the bromide derivative of compound 20 as a yellow oil (0.71 g, 1.46 mmol). The bromide derivative was taken up in methanol (3 mL) and passed through a strong anion exchange resin (DOWEX 1×8 chloride form, 200-400 mesh) eluted with methanol. After evaporation, compound 20 was obtained as a yellow oil (0.64 g, 1.45 mmol); NMR $^1$H (200 MHz, CDCl$_3$) δ 1.17 (m, 9H), 1.87 (m, 2H), 2.75-3.50 (m, 26H), 4.21 (s, 2H), 7.52 (m, 2H), 7.94 (t, 1H, J=7 Hz), 8.64 (d, 1H, J=5 Hz); ESI-MS m/z 203.15 ([M+H]$^{2+}$, 100).

Example 8: 3-(4,10-Bis(pyridin-2-ylmethyl)-1,4,7,10-tetraazacyclododecan-1-yl)-N,N,N-triethylpropan-1-aminium chloride (24)

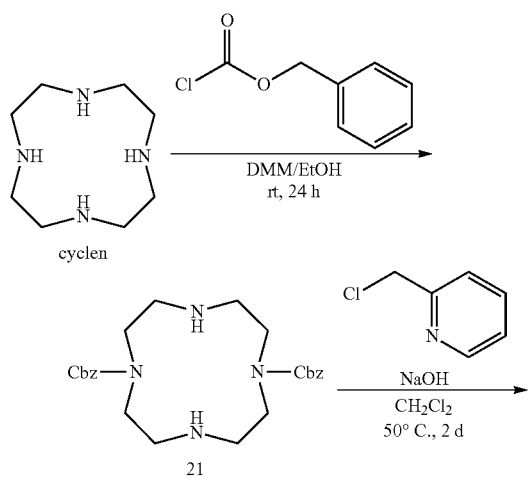

To a solution of cyclen (1.00 g, 5.80 mmol) in dimethoxymethane (60 mL) and anhydrous ethanol (25 mL) was added benzyl chloroformate (1.98 g, 11.6 mmol). The solution was stirred for 24 h at room temperature and filtered to remove solid. After evaporation under vacuum, the residue was triturated with diethyl ether (2×30 mL). The white precipitate was isolated by centrifugation and taken up with a 30% (m/m) aqueous sodium hydroxide solution (80 mL). The solution was extracted with chloroform (3×100 mL). The combined organic layers were dried over sodium sulfate, filtered and evaporated under reduced pressure to afford compound 21 as a yellow oil (2.07 g, 4.70 mmol); NMR $^1$H (200 MHz, CDCl$_3$) δ 2.93 (m, 8H), 3.60 (m, 8H), 5.17 (s, 4H), 7.35 (s, 10H).

To a solution of compound 21 (1.76 g, 4.00 mmol) in dichloromethane (20 mL) was added a 1 M aqueous sodium hydroxide solution (20 mL). The resulting biphasic mixture was vigorously stirred for 30 min before a solution of 2-chloromethylpyridine hydrochloride (1.41 g, 8.60 mmol) in dichloromethane (35 mL) was added dropwise. The mixture was heated to 50° C. for 2 d while being vigorously stirred. After cooling to room temperature, the organic phase was isolated and the aqueous phase was extracted with dichloromethane (2×20 mL). The combined organic layers were dried over sodium sulfate, filtered and evaporated under reduced pressure. The oily yellow-orange residue was purified by column chromatography on alumina with dichloromethane/methanol solution (98/2, v/v) as eluent to give compound 22 as a colorless oil (1.57 g, 2.52 mmol); NMR $^1$H (200 MHz, CDCl$_3$) δ 2.71 (br s, 8H), 3.42 (br s, 8H), 3.76 (s, 4H), 4.93 (s, 4H), 7.13 (br s, 4H), 7.29 (br s, 10H), 7.54 (t, 2H, J=7 Hz), 8.49 (br s, 2H).

Compound 22 (1.02 g, 1.64 mmol) was hydrogenated over 10% palladium on carbon (200 mg) and at atmospheric pressure in methanol (25 mL). The resulting suspension was filtered through a celite 545 pad and the filtrate was evaporated under reduced pressure. The obtained oil was purified by column chromatography on alumina with dichloromethane/methanol solution (98/2, v/v) as eluent to give compound 23 as a colorless oil (0.45 g, 1.27 mmol); NMR $^1$H (400 MHz, CDCl$_3$) δ 2.67 (s, 16H), 3.79 (s, 4H), 7.16 (t, 2H, J=6 Hz), 7.52 (d, 2H, J=8 Hz), 7.67 (t, 2H, J=8 Hz), 8.52 (d, 2H, J=5 Hz); NMR $^{13}$C (100 MHz, CDCl$_3$) δ 45.4, 52.3, 61.7, 122.3, 123.1, 136.6, 149.2, 159.8.

A solution of compound 23 (0.21 g, 0.59 mmol) and N,N,N-triethyl-3-bromopropan-1-aminium bromide (0.16 g, 0.53 mmol) in deionized water (20 mL) was stirred for 15 h at 80° C. After solvent evaporation under reduced pressure, the oily residue was purified by column chromatography on alumina with dichloromethane/methanol solution (98/2 to 95/5, v/v) as eluent to give in order of elution:

starting compound 23 (R$_f$=0.28, CH$_2$Cl$_2$/MeOH, 95/5, Al$_2$O$_3$) (0.076 g, 0.21 mmol)

bromide derivative of compound 24 (R$_f$=0.05, CH$_2$Cl$_2$/MeOH, 95/5, Al$_2$O$_3$) as a yellow oil (0.115 g, 0.20 mmol).

The bromide derivative of 24 was taken up in methanol (2 mL) and passed through a strong anion exchange resin (DOWEX 1×8 chloride form, 200-400 mesh) eluted with methanol. After evaporation under vacuum, compound 24 was obtained as a yellow oil (0.10 g, 0.19 mmol); NMR $^1$H (500 MHz, D$_2$O) δ 1.06 (t, 9H, J=7 Hz), 1.25 (m, 2H), 1.64 (m, 2H), 1.99 (m, 2H), 2.49 (s, 8H), 2.82 (s, 4H), 3.07 (m, 10H), 3.77 (s, 4H), 7.44 (t, 2H, J=6 Hz), 7.55 (d, 2H, J=8 Hz), 7.93 (t, 2H, J=8 Hz), 8.50 (d, 2H, J=5 Hz); NMR $^{13}$C (125 MHz, D$_2$O) δ 6.7, 21.7, 43.2, 46.6, 48.7, 48.9, 50.0, 52.6, 54.5, 61.6, 123.3, 125.5, 138.1, 148.1, 158.1.

Example 9: N,N,N-Triethyl-3-(8-(pyridin-2-ylmethyl)-1,4,8,11-tetraazacyclotetradecan-1-yl)propan-1-aminium chloride (27)

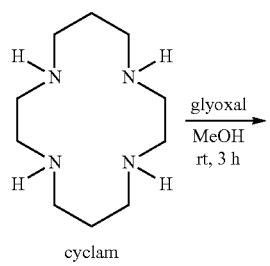

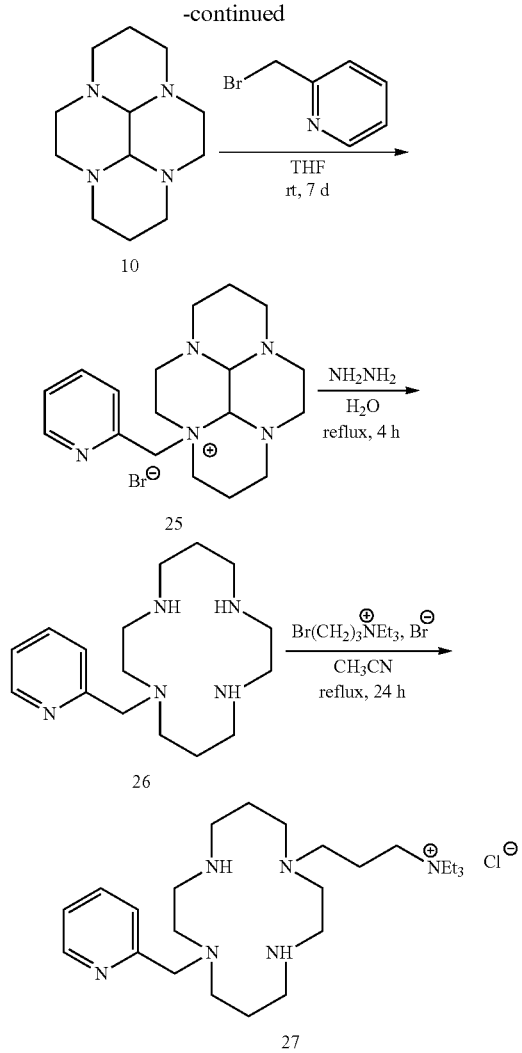

Synthesis of compound 10 was described in example 4.

2-(bromomethyl)pyridine hydrobromide (1.37 g, 5.42 mmol) in 2 M aqueous potassium carbonate solution (20 mL) was rapidly extracted with diethyl ether (3×20 mL). The combined organic layers were dried over sodium sulfate, filtered and evaporated under reduced pressure to give the 2-(bromomethyl)pyridine which was immediately taken up with anhydrous tetrahydrofuran (20 mL) and added to a solution of compound 10 (1.00 g, 4.50 mmol) in anhydrous tetrahydrofuran (20 mL). The solution was stirred for 7 d at room temperature under an argon atmosphere. The red precipitate was filtered, washed with anhydrous tetrahydrofuran (20 mL), dried under vacuum to give compound 25 as a pink solid (426 mg, 1.08 mmol); NMR $^1$H (200 MHz, D$_2$O) δ 1.42 (d, 1H, J=15 Hz), 1.74 (d, 1H, J=15 Hz), 2.26 (m, 4H), 2.50 (m, 2H), 3.08 (m, 6H), 3.48 (m, 4H), 3.74 (s, 1H), 3.78 (m, 1H), 4.24 (td, 1H, J=12 Hz, 3 Hz), 4.33 (s, 1 Hz), 4.73 (d, 1H, J=13 Hz), 5.07 (d, 1H, J=13 Hz), 7.57 (td, 1H, J=6 Hz, 3 Hz), 7.67 (d, 1H, J=9 Hz), 7.96 (td, 1H, J=9 Hz, 3 Hz), 8.65 (d, 1H, J=6 Hz); NMR $^{13}$C (50 MHz, D$_2$O) δ 20.6, 21.0, 44.5, 49.2, 52.0, 53.9, 54.5, 55.9, 56.6, 63.1, 65.5, 72.1, 84.8, 128.4, 131.6, 141.2, 149.2, 152.9; ESI-MS m/z 314.25 ([MH]$^+$, 100).

A solution of compound 25 (383 mg, 0.96 mmol) in hydrazine monohydrate (15 mL) was refluxed for 4 h and then cooled to 0° C. overnight. The precipitate was filtered and taken up with ethanol (20 mL). After evaporation under reduced pressure, compound 26 was obtained as a yellow oil (180 mg, 0.62 mmol); NMR $^1$H (200 MHz, CDCl$_3$) δ 1.70 (m, 2H), 1.87 (m, 2H), 2.50-2.95 (m, 19H), 3.71 (s, 2H), 7.13 (t, 1H, J=6 Hz), 7.58 (d, 1H, J=8 Hz), 7.65 (t, 1H, J=8 Hz), 8.50 (d, 1H, J=5 Hz); NMR $^{13}$C (50 MHz, CDCl$_3$) δ 26.4, 28.7, 47.6, 48.0, 49.0, 49.3, 49.6, 51.0, 54.1, 55.6, 59.9, 122.3, 123.4, 136.6, 149.2, 159.8; ESI-MS m/z 292.23 ([MH]$^+$, 100).

A solution of compound 26 (0.18 g, 0.62 mmol) and N,N,N-triethyl-3-bromopropan-1-aminium bromide (0.19 g, 0.63 mmol) in anhydrous acetonitrile (15 mL) was refluxed for 24 h. After cooling to room temperature and solvent evaporation under reduced pressure, the residue was purified by column chromatography on alumina with dichloromethane/methanol solution (90/10, v/v) to afford the bromide derivative of compound 27 as a orange oil (0.26 g, 0.51 mmol). The bromide derivative was taken up in methanol (2 mL) and passed through a strong anion exchange resin (DOWEX 1×8 chloride form, 200-400 mesh) eluted with methanol. After evaporation under reduced pressure, compound 27 was obtained as a orange oil (0.23 g, 0.49 mmol); NMR $^1$H (200 MHz, D$_2$O) δ 1.19 (t, 9H, J=7 Hz), 1.61 (m, 2H), 1.84 (m, 4H), 2.61 (m, 12H), 2.77 (s, 6H), 3.20 (q, 6H, J=7 Hz), 3.29 (s, 2H), 3.65 (s, 2H), 7.31 (t, 1H, J=6 Hz), 7.42 (m, 1H), 7.82 (t, 1H, J=6 Hz), 8.42 (t, 1H, J=6 Hz); NMR $^{13}$C (50 MHz, D$_2$O) δ 7.3, 16.4, 24.3, 46.2, 49.3, 50.6, 51.6, 52.1, 52.9, 53.2, 53.9, 55.3, 59.3, 123.7, 125.3, 138.6, 149.2, 158.1; ESI-MS m/z 433.48 ([M]$^+$, 100).

Example 10: 3-(4,11-Bis(pyridin-2-ylmethyl)-1,4,8,11-tetraazacyclotetradecan-1-yl)-N,N,N-triethylpropan-1-aminium chloride (30)

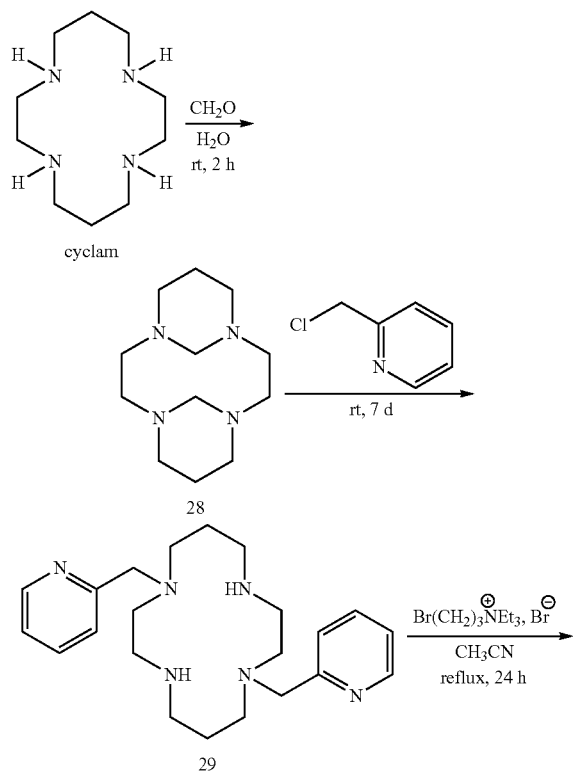

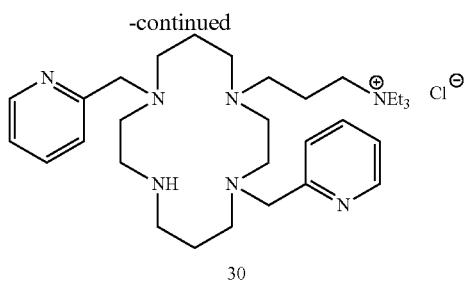

To a solution of cyclam (0.50 g, 2.50 mmol) in deionized water (20 mL) was rapidly added a 37% (m/m) aqueous solution of formaldehyde (0.51 mL, 5.0 mmol). The mixture was stirred for 2 h at room temperature. The white precipitate was filtered, washed with desionized water (20 mL) and dried under vacuum to give compound 28 as a white solid (0.47 g, 2.10 mmol); NMR $^1$H (200 MHz, CDCl$_3$) δ 1.14 (m, 1H), 1.21 (m, 1H), 2.12-2.48 (m, 2H), 2.37 (d, 4H, J=10 Hz), 2.62 (td, 4H, J=12 Hz, 3 Hz), 2.72-2.90 (m, 4H), 2.90 (d, 2H, J=10 Hz), 3.14 (d, 4H, J=10 Hz), 5.44 (dt, 2H, J=10 Hz, 1 Hz); NMR $^{13}$C (50 MHz, CDCl$_3$) δ 20.2, 49.3, 53.6, 68.9; ESI-MS m/z 225.20 ([MH]$^+$, 100).

2-(chloromethyl)pyridine hydrochloride (0.71 g, 5.60 mmol) in 4 M aqueous sodium hydroxide solution (20 mL) was extracted with dichloromethane (3×20 mL). The combined organic layers were dried over sodium sulfate, filtered and evaporated under reduced pressure to afford the unstable 2-(chloromethyl)pyridine. To a solution of this reagent in anhydrous acetonitrile (20 mL) was added a solution of compound 28 (0.31 g, 1.40 mmol) in anhydrous acetonitrile (20 mL). The resulting solution was stirred for 7 d at room temperature under an argon atmosphere then a 3 M aqueous sodium hydroxide solution (20 mL) was added. The solution was stirred for additional 15 h at room temperature, extracted with dichloromethane (3×50 mL). The combined organic layers were dried over sodium sulfate, filtered, evaporated under reduced pressure to give compound 29 as a red oil (0.48 g, 1.25 mmol); NMR $^1$H (500 MHz, CDCl$_3$) δ 1.88 (quint, 4H, J=8 Hz), 2.58 (t, 4H, J=6 Hz), 2.70-2.90 (m, 12H), 3.30 (br s, 2H) 3.78 (s, 4H), 7.07 (td, 2H, J=8 Hz, 1 Hz), 7.34 (d, 2H, J=8 Hz), 7.56 (td, 2H, J=8 Hz, 2 Hz), 8.46 (d, 2H, J=7 Hz); NMR $^{13}$C (125 MHz, CDCl$_3$) δ 25.3, 47.0, 49.3, 52.1, 53.6, 59.1, 121.6, 123.0, 135.9, 148.6, 158.0; ESI-MS m/z 383.25 ([M+H]$^+$, 100), 192.08 ([M+2H]$^{2+}$, 60).

A solution of compound 29 (0.31 g, 0.81 mmol) and N,N,N-triethyl-3-bromopropan-1-aminium bromide (0.25 g, 0.81 mmol) in anhydrous acetonitrile (15 mL) was refluxed for 24 h. After cooling to room temperature and evaporation under reduced pressure, the residue was purified by column chromatography on alumina with dichloromethane/methanol solution (90/10, v/v) as eluent to give the bromide derivative of compound 30 as a yellow oil (0.13 g, 0.22 mmol). The bromide derivative of 30 was taken up in methanol (2 mL) and passed through a strong anion exchange resin (DOWEX 1×8 chloride form, 200-400 mesh)

eluted with methanol. After evaporation under vacuum, compound 30 was obtained as a yellow oil (84 mg, 0.15 mmol); NMR $^1$H (500 MHz, D$_2$O) δ 1.29 (m, 9H), 1.83 (m, 4H), 1.91 (m, 2H), 2.55-3.00 (m, 12H), 3.07 (tt, 2H, J=14 Hz, 8 Hz), 3.20-3.50 (m, 12H), 3.75 (s, 2H), 3.82 (s, 2H), 7.35 (m, 2H), 7.47 (m, 2H), 7.80 (m, 2H), 8.48 (m, 2H); NMR $^{13}$C (125 MHz, D$_2$O) δ 6.6, 24.2, 28.2, 45.7, 48.2, 51.9, 52.4, 52.7, 53.2, 54.3, 54.6, 58.7, 122.8, 123.8, 137.6, 148.3, 157.5; ESI-MS m/z 262.72 ([M+H]$^{2+}$, 100).

B. Radiolabelling

The $^{64}$Cu radionuclide was produced at cyclotron of CEMHTI (Conditions Extrêmes et Matériaux: Haute Temperature et Irradiation, UPR3079 CNRS, Orléans, France) as [$^{64}$Cu]CuCl$_2$ in a 0.1 M aqueous hydrochloric acid solution. The $^{64}$Cu production was obtained through the $^{64}$Ni(p,n)$^{64}$Cu nuclear reaction. The target is a $^{64}$Ni layer isotopically enriched to 99.6% electroplated on gold backing. After bombardment, the nickel layer was dissolved in hot 2 M aqueous nitric acid solution and evaporated to dryness. The resulting residue was dissolved in 9.36 M aqueous hydrochloric acid solution (2 mL) and purified by column chromatography on an anion exchange resin (Bio-Rad AG 1-×8, 4×1 cm) conditioned with 9.36 M hydrochloric acid prior to use. Separation of Ni and Co was achieved by successive washing with a 10 M hydrochloric acid solution and a mixture of 0.3 M hydrochloric acid and ethanol (28/72, v/v), respectively. Then the copper was eluted using water (10 mL). The obtained solution was evaporated to dryness and then dissolved in a small amount of 0.1 M hydrochloric acid solution. Radionuclidic purity for $^{64}$Cu was measured using a calibrated high purity Ge detector and was found to be better than 99% (Amiot M. N. et al. *Nucl. Instrum. Methods Phys. Res. A* 2012, 684, 97-104).

Radiolabelling was performed in a hot cell located in a dedicated room. Same radiolabelling conditions were used for all ligands:

In a vial, [$^{64}$Cu]CuCl$_2$ in 0.10 M aqueous hydrochloric acid solution (2 μL, i.e. around 3 MBq) was added to prepared solution of 5 mM aqueous solution of ligand (compounds of formula (I')) (20 μL) in 0.10 M sodium citrate buffer (pH 6.0) (200 μL). The vial was placed in a temperature-controlled stainless steel vat.

Radiochemical purity and composition of $^{64}$Cu-complexes were controlled by radio-TLC on glass microfiber chromatography paper impregnated with a silica gel (Agilent ITLC-SG) using a mobile phase 5 M ammonium acetate/methanol solution at variable ratio (70/30 to 30/70 preferentially 50/50, v/v). An aliquot (2 μL) of the crude mixture was deposited on ITLC-SG plate. An aliquot (2 μL) of a blank sample, prepared from a solution of [$^{64}$Cu]CuCl$_2$ in 0.10 M aqueous hydrochloric acid solution (2 μL, i.e. around 3 MBq) and 0.10 M sodium citrate buffer (pH 6.0) (220 μL), was simultaneously deposited on the same plate for comparison. ITLC-SG were eluted and then recorded with an AMBIS radioanalytic imaging system (AMBIS Systems, San Diego, Calif.). With above-mentioned conditions, free $^{64}$Cu migrated at the front of the plate. The complete complexation of $^{64}$Cu with ligands was then monitored by the disappearance of the front spot.

TABLE 1

Optimal conditions for $^{64}$Cu-radiolabelling

| Bifunctional chelator (ligand) | Reaction time (min) | Temperature (° C.) | Radiochemical purity (%) | Eluent composition: AcONH$_4$ (5M)/ MeOH v/v; R$_f$ | Radiolabelled compound |
|---|---|---|---|---|---|
| 2 | 15 | 25 | 99.9 | 50/50; 0.32 | $^{64}$Cu-2 |
| 5 | 15 | 30 | 87.1 | 50/50; 0.32 | $^{64}$Cu-5 |
| 9 | 15 | 25 | 99.0 | 70/30; 0.29 | $^{64}$Cu-9 |
| 13 | 30 | 70 | 99.9 | 50/50; 0.21 | $^{64}$Cu-13 |
| 14 | 30 | 70 | 99.9 | 50/50; 0.28 | $^{64}$Cu-14 |
| 16 | 30 | 50 | 99.9 | 70/30; 0.62 | $^{64}$Cu-16 |
| 20 | 30 | 30 | 95.5 | 50/50; 0.20 | $^{64}$Cu-20 |
| 24 | 30 | 30 | 96.6 | 50/50; 0.22 | $^{64}$Cu-24 |
| 27 | 15 | 30 | 94.2 | 50/50; 0.17 | $^{64}$Cu-27 |
| 30 | 15 | 50 | 89.4 | 50/50; 0.19 | $^{64}$Cu-30 |

These conditions have been applied for the radiolabelled ligand biodistributions and imaging studies. Before animal injection, radiochemical purity of each solution was controlled with the radio-ITLC procedure described above.

C. Biodistribution

Quantitative biodistribution of radiolabelled compounds was determined in rats: healthy animals as well as rats with primary grade II orthotopic chondrosarcoma at stage Day-30 after induction. The chondrosarcoma model was the Swarm Rat Chondrosarcoma model (SRC) implanted in paratibial location. Radiolabelled compounds (5-10 Mbq/animal) were i.v. administered in the caudal vein of animals being anesthetized of mixture of ketamine (58 mg/kg i.p.) (Imalgéne 500®) and xylazine (6 mg/kg i.p.) (Rompun® 2%, Bayer, France). One hour after injection, animals were then sacrificed by CO$_2$ inhalation, dissected and organs of interest removed, weighed and their radioactivity counted using a gamma counter (Model 1480 Wizard, Perkin Elmer Life Sciences, Boston, USA). Organs collected were blood, muscle, knee, kidneys, liver, thoracic ribs, bladder for both healthy and chondrosarcoma bearing rats. For SRC animals, tumour was also sampled. After radioactive decay correction, results were expressed for each organ as % injected dose per gram (% ID/g) and averaged per group.

TABLE 2

Biodistribution in healthy and SRC bearing rats at 1 h after i.v. injection of radiolabelled compounds. Results are expressed in % ID/g and presented as mean ± SD (n = 3).

|  | Liver | Articular cartilage | Muscle | Kidney | Blood | Tumor | Bladder |
| --- | --- | --- | --- | --- | --- | --- | --- |
| $^{64}$Cu-2 | ND | 2.6 ± 1.1 | 0.4 ± 0.3 | 16.4 ± 6.6 | 0.1 ± 0.05 | 3.5 ± 0.5 | 62.2 ± 17.6 |
| $^{64}$Cu-5 | — | 5.9 ± 2.3 | 1.5 ± 1.2 | 27.5 ± 10.1 | 0.8 ± 1.2 | 5.2 ± 2.1 | 66.5 ± 14.4 |
| $^{64}$Cu-13 | 0.06 ± 0.01 | 0.16 ± 0.06 | 0.03 ± 0.01 | 1.06 ± 0.66 | 0.07 ± 0.01 | NA | 11.83 ± 5.57 |
| $^{64}$Cu-14 | 0.06 ± 0.02 | 0.11 ± 0.02 | 0.04 ± 0.00 | 0.73 ± 0.22 | 0.09 ± 0.04 | NA | 14.71 ± 7.12 |
| $^{64}$Cu-27 | 1.2 ± 0.4 | 1.5 ± 0.4 | 0.43 ± 0.15 | 7.6 ± 4.6 | 0.4 ± 0.07 | 1.4 ± 0.07 | 30.5 ± 10.9 |
| $^{64}$Cu-30 | — | 2.7 ± 0.4 | 0.80 ± 0.4 | 9.2 ± 0.9 | 0.7 ± 0.2 | 4.2 ± 0.6 | 25.2 ± 10.6 |

NA: not applicable
ND: at undetectable levels
—: not determined

D. In Vivo PET Imaging

An in vivo PET acquisition was performed on animals (n=2-3 animals/compound) at a delay of 1 h after i.v. injection of each radiolabelled compound (12 MBq/animal). In vivo imaging consisted in a 5 bed-positions acquisition, for a total time of 50 min with an energy window set at 250-700 keV, and using a small animal dedicated device (Explore Vista®, GE Healthcare). Image reconstruction used an ordered-subset expectation maximization (FORE/2D OSEM) method including corrections for scanner dead time and scattered radiation. Scans were quantitatively analyzed using eXplore VISTA® workspace.

A comparative in vivo PET imaging was carried out with the radiolabeled compound $^{64}$Cu-2 and $^{99m}$Tc-NTP 15-5.

The in vivo imaging was determined in 3 healthy New Zealand rabbits (14 weeks old, 3.5 kg weight, Charles River, France), being randomly divided into two groups:
- one group receiving $^{99m}$Tc-NTP 15-5: 80 MBq/animal for in vivo imaging;
- one group receiving $^{64}$Cu-2: 120 MBq/animal for in vivo imaging.

Three animals were submitted to serial in vivo imaging (planar and SPECT-CT acquisition for $^{99m}$Tc-NTP 15-5 and PET-CT acquisition for $^{64}$Cu-NTP 15-5), with each animal being examined at 15 min, 1 h, 3 h, 6 h and 24 h if applicable. For in vivo planar, SPECT-CT and PET-CT imaging, anesthetized animals were placed on prone position.

Acquisition Parameters were:
For $^{99m}$Tc-NTP 15-5 Imaging:
Using the SPECT-CT Camera (Symbia®, Siemens) planar imaging consisted in a 300 s duration acquisition and a 256×256 matrix.

For SPECT, 32 projections were acquired, with the duration of each projection being 20 s. For CT, 2-mm thick CT slices (80 kV, 30 mAs,) were acquired and automatically fused with SPECT slices.

For $^{64}$Cu-NTP 15-5 imaging:
In vivo imaging consisted in a 5 bed-position acquisition, 4 min-duration each.

For CT, 2-mm thick CT slices (120 kV, 30 mAs,) were acquired and automatically fused with PET slices.

Results:
The obtaining of images with a higher contrast was observed with the use of $^{64}$Cu-2 compared to the use of $^{99m}$Tc-NTP15-5

Besides, it was also shown that the cartilages of the studied animals were still visible in PET 24 h after the injection of $^{64}$Cu-2 whereas 6 h after the injection of $^{99m}$Tc-NTP15-5 with SPECT, the cartilages cannot be distinguished anymore.

E. Comparative Study of Biodistribution with $^{99m}$Tc-NTP 15-5 and $^{99m}$Tc-NTPC Study 1:
The following table discloses the biodistribution of $^{99m}$Tc-NTP 15-5 in healthy rat, carried out in similar conditions than those of the compounds of the invention (see section C above).

| Organ | % ID/g[a] |
| --- | --- |
| Blood | 0.90 ± 0.08 |
| Lung | 1.71 ± 0.97 |
| Liver | 2.02 ± 0.38 |
| Spleen | 0.71 ± 0.25 |
| Kidney | 15.4 ± 12.5 |
| Muscle | 0.37 ± 0.24 |
| Tibial plateau | 2.99 ± 1.60 |
| Bone (tibia) | 0.51 ± 0.29 |
| Testis | 1.11 ± 0.47 |
| Brain | 0.14 ± 0.02 |

[a]Data are presented as an average from 3 animals ± SD. All animals were injected with 0.37 MBq (200 μL) of $^{99m}$Tc-NTP 15-5. Rats were euthanized by CO$_2$ inhalation 1 h p.i.

Study 2:
Biodistribution were determined in 36 healthy New Zealand rabbits (18 males and 18 females, 14 weeks old, 3.5 kg weight, Charles River, France), being randomly divided into two groups:
- One group receiving $^{99m}$Tc-NTP 15-5: 18±3 MBq/animal for biodistribution;
- One group receiving $^{64}$Cu-2: 17±4 MBq/animal for biodistribution.

The compounds were i.v. administered to anesthetized animals (ketamine/xylazine by intramuscular route) in the marginal ear vein.

At selected time points after injection (15 min, 1 h, 3 h, 6 h, 20 h after injection), animals (3 animals/time point/compound) were sacrificed by a lethal i.v. dose of pentobarbital. Organs of interest were dissected, weighed and their radioactivity measured using a gamma counter (Model 1480 Wizard, Perkin Elmer Life Sciences, Boston, USA). After radioactive decay correction, results were expressed for each organ as % injected dose per gram (% ID/g) and averaged per group and per time point.

The results are provided in the following tables:

TABLE 3

$^{64}$Cu-2

| Organs (% ID/g) | 15 min | 1 h | 3 h | 6 h | 20 h |
|---|---|---|---|---|---|
| Blood | 0.31 ± 0.17 | 0.08 ± 0.02 | 0.02 ± 0.00 | 0.02 ± 0.02 | 0.00 ± 0.00 |
| Muscle | 0.03 ± 0.02 | 0.01 ± 0.00 | 0.00 ± 0.00 | 0.00 ± 0.00 | 0.00 ± 0.00 |
| Articular Cartilage | 8.46 ± 6.18 | 4.81 ± 1.16 | 2.31 ± 0.32 | 1.00 ± 1.02 | 0.10 ± 0.02 |
| Bone | 0.07 ± 0.02 | 0.01 ± 0.00 | 0.01 ± 0.00 | 0.00 ± 0.00 | 0.00 ± 0.00 |
| Bone Marrow | 0.08 ± 0.04 | 0.03 ± 0.01 | 0.01 ± 0.00 | 0.01 ± 0.01 | 0.00 ± 0.00 |
| Thyroid | 0.11 ± 0.08 | 0.03 ± 0.01 | 0.04 ± 0.05 | 0.00 ± 0.00 | 0.00 ± 0.00 |
| Liver | 0.11 ± 0.03 | 0.04 ± 0.01 | 0.02 ± 0.00 | 0.02 ± 0.02 | 0.00 ± 0.00 |
| Kidney | 0.65 ± 0.47 | 0.26 ± 0.07 | 0.22 ± 0.01 | 0.26 ± 0.14 | 0.06 ± 0.01 |
| Urine | 1.51 ± 2.22 | 1.69 ± 2.14 | 0.92 ± 0.63 | 6.90 ± 7.93 | 0.25 ± 0.22 |
| Bile | 0.07 ± 0.04 | 0.03 ± 0.02 | 0.11 ± 0.17 | 0.02 ± 0.02 | 0.01 ± 0.00 |
| Spleen | 0.11 ± 0.08 | 0.03 ± 0.01 | 0.02 ± 0.00 | 0.02 ± 0.02 | 0.01 ± 0.00 |
| Lung | 0.23 ± 0.14 | 0.07 ± 0.02 | 0.03 ± 0.00 | 0.02 ± 0.02 | 0.00 ± 0.00 |
| Uptake ratio | 15 min | 1 h | 3 h | 6 h | 20 h |
| Cartilage/Muscle | 282 | 484 | — | — | — |
| Cartilage/Bone | 120 | 484 | — | — | — |

TABLE 4

$^{99m}$Tc-NTP 15-5

| Organs | 15 min | 1 h | 3 h | 6 h | 20 h |
|---|---|---|---|---|---|
| Blood | 1.09 ± 0.81 | 0.75 ± 0.09 | 0.17 ± 0.81 | 0.03 ± 0.00 | 0.00 ± 0.00 |
| Muscle | 0.01 ± 0.00 | 0.00 ± 0.00 | 0.00 ± 0.00 | 0.00 ± 0.00 | 0.00 ± 0.00 |
| Articular Cartilage | 1.03 ± 0.4 | 0.92 ± 0.4 | 0.35 ± 0.15 | 0.09 ± 0.03 | 0.04 ± 0.01 |
| Bone | 0.02 ± 0.01 | 0.02 ± 0.00 | 0.00 ± 0.00 | 0.00 ± 0.00 | 0.00 ± 0.00 |
| Bone Marrow | 0.02 ± 0.02 | 0.01 ± 0.00 | 0.00 ± 0.00 | 0.00 ± 0.00 | 0.00 ± 0.00 |
| Thyroid | 0.05 ± 0.04 | 0.06 ± 0.03 | 0.11 ± 0.01 | 0.02 ± 0.03 | 0.00 ± 0.00 |
| Liver | 0.05 ± 0.02 | 0.06 ± 0.03 | 0.08 ± 0.02 | 0.06 ± 0.01 | 0.03 ± 0.02 |
| Kidney | 0.19 ± 0.03 | 0.10 ± 0.06 | 0.09 ± 0.03 | 0.06 ± 0.01 | 0.07 ± 0.00 |
| Urine | 1.40 ± 1.02 | 4.08 ± 5.75 | 1.34 ± 0.52 | 1.61 ± 0.6 | 0.40 ± 0.01 |
| Bile | 0.09 ± 0.08 | 0.09 ± 0.07 | 0.18 ± 0.24 | 0.08 ± 0.02 | 0.03 ± 0.01 |
| Spleen | 0.03 ± 0.06 | 0.02 ± 0.01 | 0.00 ± 0.00 | 0.00 ± 0.00 | 0.01 ± 0.00 |
| Lung | 0.04 ± 0.04 | 0.02 ± 0.00 | 0.01 ± 0.00 | 0.00 ± 0.00 | 0.00 ± 0.00 |
| Uptake ratio | 15 min | 1 h | 3 h | 6 h | 20 h |
| Cartilage/Muscle | 103 | — | — | — | — |
| Cartilage/Bone | 51.5 | 46 | — | — | — |

It was shown that the $^{64}$Cu-2 of the invention advantageously allows a faster and higher uptake into the cartilages (which are the target organs) compared to $^{99m}$Tc-NTP 15-5. More particularly, a higher cartilage/muscle and cartilage/Bone ratios are obtained with $^{64}$Cu-2 compared to $^{99m}$Tc-NTP 15-5. These ratios are at the origin of a highly contrasted imaging from 15 min to 24 h pi of $^{64}$Cu-2.

As shown in FIG. 1 and as extracted from tables 3 and 4, $^{64}$Cu-2 was observed to rapidly accumulate in cartilage as early as 15 min p.i. For each time investigated, $^{64}$Cu-2 accumulated in cartilage at higher levels than $^{99m}$Tc-NTP 15-5. Moreover, cartilage retention could be still imaged in vivo at 24 h p.i. with $^{64}$Cu-2, whereas no satisfying images could be acquired after 6 h pi with $^{99m}$Tc-NTP 15-5.

Figure 2:
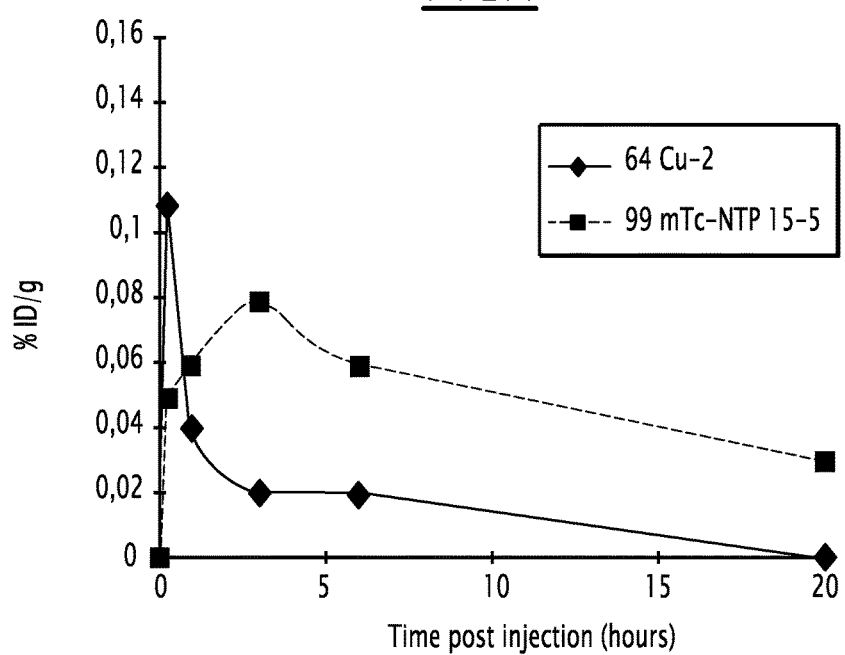
FIG. 2 represents the comparison of the liver accumulation of $^{64}Cu$-2 and $^{99m}Tc$-NTP 15-5 in healthy rabbits. It describes the percentage of ID/g of liver for each compound in function of the time post injection (p.i.) (in hours).

Differences in liver accumulation were observed between $^{64}$Cu-2 and $^{99m}$Tc-NTP 15-5 (FIG. 2 and data extracted from tables 3 and 4). First, the liver uptake is clearly low for the studied compounds, which indicates that $^{64}$Cu-2 is stable given that the in vivo release of $^{64}$Cu from transchelation or transmetalation is negligible. Second, liver accumulation appeared to be shorter with $^{64}$Cu-2, which is clearly required for imaging agents. This very low liver accumulation was notably surprising as it is known from Yu et al. ("Biodistibution of [$^{64}$Cu]Cu$^{2+}$ and variance of metallothionein during tumor treatment by cancer", Nuclear Medicine and Biology, Vol. 25, p. 111-116, 1998) that complexes comprising 64Cu typically lead to high liver uptake.

Moreover, accumulation in kidneys was observed to be significantly higher with $^{64}$Cu-2 respectively to $^{99m}$Tc-NTP 15-5. The accumulation in kidneys is notably interesting as it indicates a high/rapid urinary elimination of $^{64}$Cu-2.

Study 3:

Quantitative biodistribution of radiolabelled compounds was determined in rats: healthy animals as well as rats with primary grade II orthotopic chondrosarcoma at stage Day-30 after induction. The chondrosarcoma model was the Swarm Rat Chondrosarcoma model (SRC) implanted in paratibial location. Radiolabelled compounds (5-10 Mbq/animal) were i.v. administered in the caudal vein of animals being anesthetized of mixture of ketamine (58 mg/kg i.p.) (Imalgéne 500®) and xylazine (6 mg/kg i.p.) (Rompun® 2%, Bayer, France). One hour after injection, animals were then sacrificed by CO$_2$ inhalation, dissected and organs of interest removed, weighed and their radioactivity counted using a gamma counter (Model 1480 Wizard, Perkin Elmer Life Sciences, Boston, USA). For SRC animals, tumor was also sampled. After radioactive decay correction, results were expressed for each organ as % injected dose per gram (% ID/g) and averaged per group.

The comparison was carried out between $^{64}$Cu-5 and $^{99m}$Tc-NTPC, the NTPC ligand having the following structure:

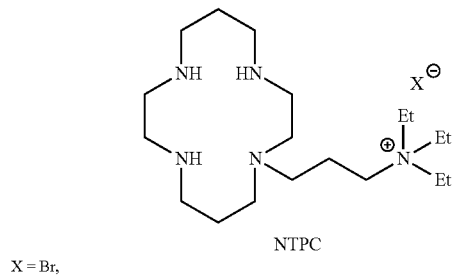

X = Br,

NTPC

The results are provided in the following table:

| Tissue | $^{99m}$Tc-NTPC[a] % ID/g | $^{64}$CU-5[b] % ID/g |
|---|---|---|
| Blood | 0.22 ± 0.05 | 0.8 ± 1.2 |
| Liver | 4.34 ± 0.47 | n.d. |
| Kidney | 2.96 ± 0.36 | 27.5 ± 10.1 |
| Intervertebral disc | 0.36 ± 0.09 | 3.5 ± 0.6 |
| Articular cartilage | 0.52 ± 0.08 | 5.9 ± 2.3 | n.d.: not determined
[a]Maurizis et al., Drug Metabolism & Dispositions 2000, 28, 418-422, 7.4 MBq/Kg
[b]5-10 MBq/animal These results show that $^{64}$Cu-5 allow higher uptake in target organs (intervertebral disc and articular cartilage) than with $^{99m}$Tc-NTPC. Besides, higher uptake in kidneys was observed with $^{64}$Cu-5 respectively to $^{99m}$Tc-NTPC. The accumulation in kidneys is notably interesting as it indicates a good elimination of $^{64}$Cu-5 over $^{99m}$Tc-NTPC.

In addition, the uptake of $^{64}$Cu-5 in liver is advantageously undetectable compared to $^{99m}$Tc-NTPC, which notably indicates that $^{64}$Cu-5 is stable as Cu is not released.

The invention claimed is:
1. Compound of formula (I):

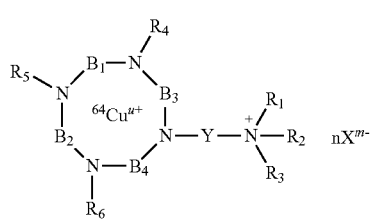

(I)

wherein:
$R_4$, $R_5$ and $R_6$ are independently of each other, chosen from the group consisting of: H, —$(CH_2)_p$COOR', —$(CH_2)_q$Ar, —$(CH_2)_q$Het and an alkyl group linear or branched comprising from 1 to 10 carbon atoms, wherein:
R' represents H, an alkyl group linear or branched comprising from 1 to 10 carbon atoms, or an aryl group comprising from 6 to 20 carbon atoms;
p and q are, independently of each other, an integer comprised from 0 to 10;

Ar represents an aryl group comprising from 6 to 20 carbon atoms;
Het represents a heteroaryl comprising from 5 to 20 atoms;
$R_1$, $R_2$ and $R_3$ represent, independently of each other, an alkyl group, linear or branched, comprising from 1 to 10 carbon atoms, or an aryl group comprising from 6 to 20 carbon atoms;
or $R_1$, $R_2$ and $R_3$ together with the nitrogen atom carrying them, form a saturated or unsaturated nitrogen-containing heterocycle, said heterocycle being optionally substituted;
or $R_4$ and $R_5$ can form together, with the nitrogen atoms carrying them, a heterocycle group comprising from 4 to 20 atoms, said heterocycle group optionally comprising at least one additional heteroatom chosen from O, N and S;
or $R_4$ and $R_6$ can form together, with the nitrogen atoms carrying them, a heterocycle group comprising from 9 to 40 atoms, said heterocycle group optionally comprising at least one additional heteroatom chosen from O, N and S;
$B_1$, $B_2$ and $B_4$ represent, independently of each other, an alkylene group comprising from 2 to 10 carbon atoms, said alkylene group being linear or branched;
$B_3$ represents

wherein:
r, s and t are, independently of each other, an integer comprised from 0 to 10;
$R_7$ is chosen from the group consisting of: H, —$(CH_2)_p$COOR', —$(CH_2)_g$Ar, —$(CH_2)_q$Het and an alkyl group linear or branched comprising from 1 to 10 carbon atoms, wherein R', Ar, Het, p and q are as defined above;
Y represents an alkylene group comprising from 1 to 10 carbon atoms;
u represents an integer comprised from 0 to 4;
n represents an integer comprised from 1 to 6;
$X^{m-}$ is a conjugate base of an acid, m representing an integer comprised from 1 to 4;
n, m and u being such that the total charge of the compound of formula (I) is zero,
wherein the aryl and the heteroaryl groups are optionally substituted by one or more substituents chosen from alkyl, alkenyl, alkynyl, alkoxy, halo, hydroxy, cyano, nitro, amino, $SO_3H$, sulphate, phosphate, perfluoroalkyl, perfluoroalkoxy, methylenedioxy, ethylenedioxy, carboxyl, oxo, thioxo, imino, $S(O)_n$, alkyl where n is 0-2, $S(O)_n$ aryl where n is 0-2, $S(O)_n$ heteroaryl where n is 0-2, $S(O)_n$ heterocyclyl where n is 0-2, amine, ester, amide, sulfonamide, unsubstituted aryl, unsubstituted heteroaryl, unsubstituted heterocyclyl, and unsubstituted cycloalkyl
or a pharmaceutically acceptable salt or hydrate thereof.

2. Compound according to claim 1, having the following formula (II):

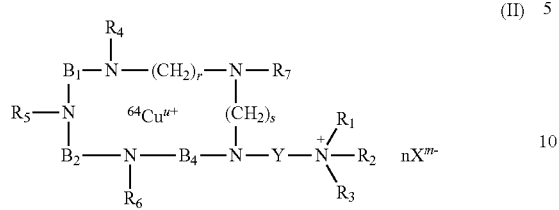
(II)

or a pharmaceutically acceptable salt or hydrate thereof.

3. Compound according to claim 1, having the following formula (III):

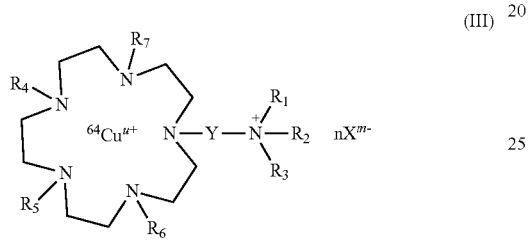
(III)

or a pharmaceutically acceptable salt or hydrate thereof.

4. Compound according to claim 3, having the following formula:

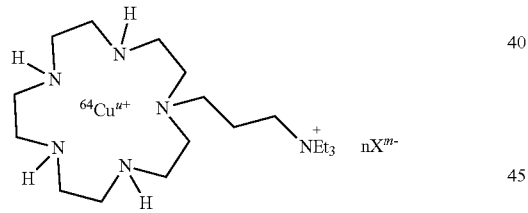

5. Compound according to claim 1, having the following formula (IV):

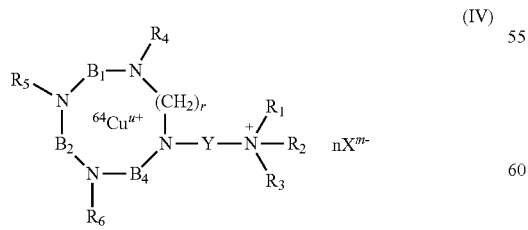
(IV)

or a pharmaceutically acceptable salt, or hydrate thereof.

6. Compound according to claim 5, having one of the following formulae (V) and (VI):

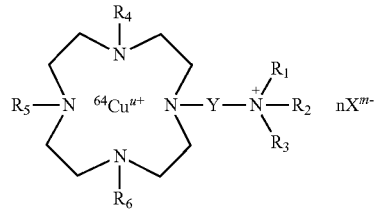
(V)

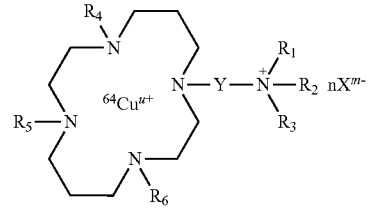
(VI)

or a pharmaceutically acceptable salt or hydrate thereof.

7. Compound according to claim 6, chosen in the group consisting in:

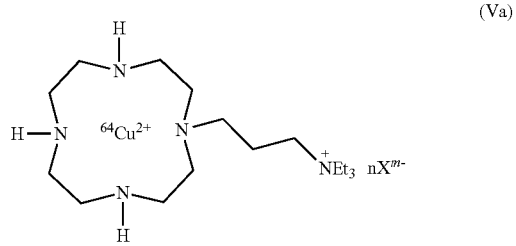
(Va)

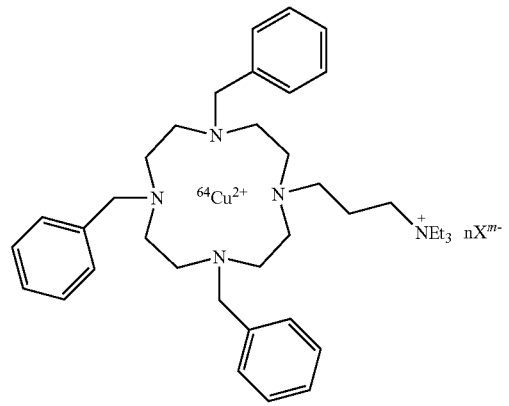
(Vb)

(Vc)

(Vd)
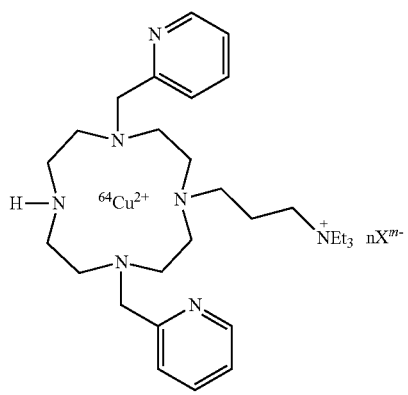

(VIa)
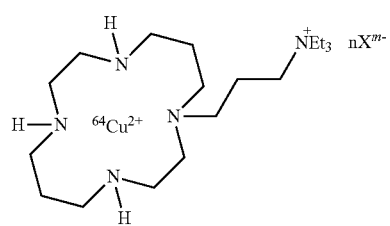

(VIb)
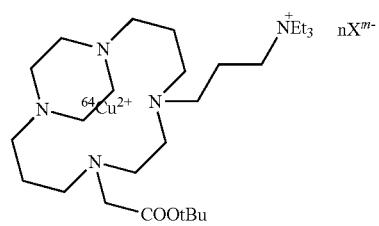

(VIc)
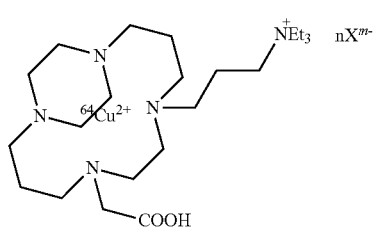

(VId)
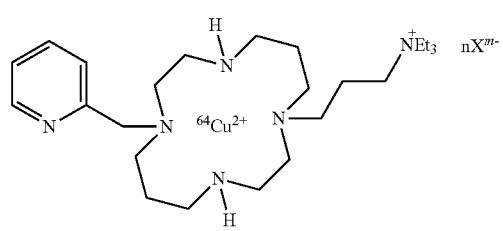

(VIe)
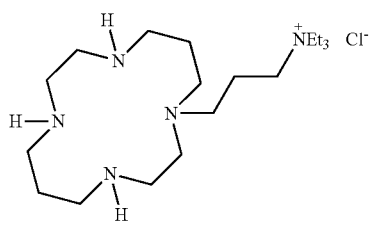

8. Process of preparation of the compound of formula (I) according to claim 1, comprising reacting a compound of formula (I')

(I')

$$\begin{array}{c}R_5\text{-N}\cdots B_1\text{-N}\cdots R_4\\ \quad\quad B_2\quad\quad B_3\\ \text{N}\text{-}B_4\text{-N}\text{-}Y\text{-}\overset{+}{N}\text{-}R_2\quad n'X^{m'-}\\ R_6\quad\quad R_3\end{array}$$

with $^{64}Cu$ in aqueous solution, wherein:

n' represents an integer comprised from 0 to 6;

m' represents an integer comprised from 1 to 3.

9. Compound of formula (I') is selected from the group consisting of:

(I'a)
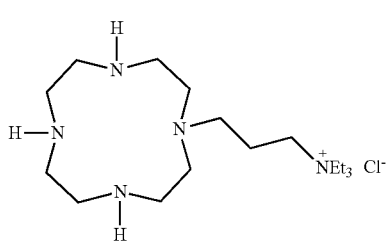

(I'b)

-continued

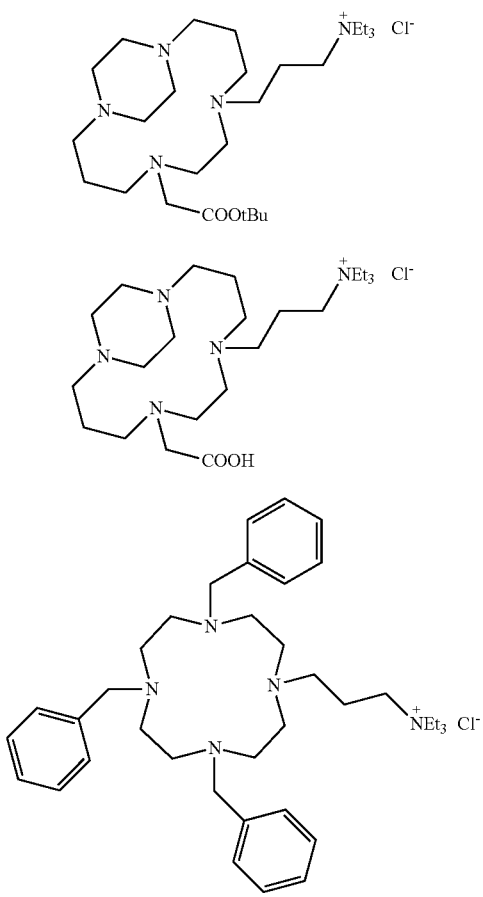

(I'c)
(I'd)
(I'e)
(I'f)
(I'g)

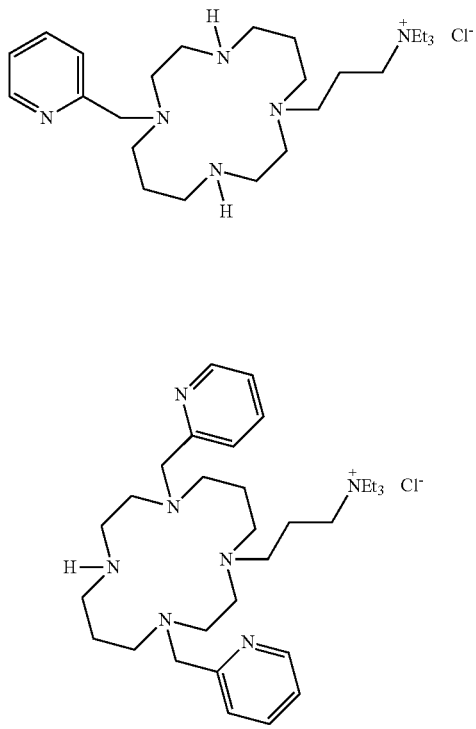

(I'h)
(I'i)

or a pharmaceutically acceptable salt thereof.

10. A kit comprising:
a) a compound of formula (I'):

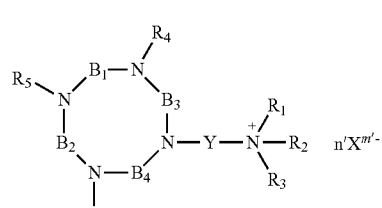

(I')

or a pharmaceutical acceptable salt thereof, and
b) a buffer solution pH=6 at 0.1 M
c) $^{64}Cu$ in solution.

11. Pharmaceutical composition comprising as active principle, a compound as defined in claim 1, and a pharmaceutically acceptable vehicle or excipient.

12. Solution comprising a compound according to claim 1, its pharmaceutically acceptable salt, or mixtures thereof.

13. A method of PET imaging comprising administering to a mammal an effective amount of a compound as defined in claim 1, or one of its pharmaceutically acceptable salts.

* * * * *